(12) United States Patent
Lee et al.

(10) Patent No.: US 8,772,284 B2
(45) Date of Patent: *Jul. 8, 2014

(54) METHOD OF TREATING CANCER USING COMBINATION OF A BIFUNCTIONAL ALKYLATING AGENT AND DNA REPAIR INHIBITORS

(75) Inventors: Te-Chang Lee, Taipei (TW); Tsann-Long Su, Xizhi (TW); Ting-Chao Chou, Paramus, NJ (US)

(73) Assignee: Academia Sinica, Taipei (TW)

( * ) Notice: Subject to any disclaimer, the term of this patent is extended or adjusted under 35 U.S.C. 154(b) by 115 days.

This patent is subject to a terminal disclaimer.

(21) Appl. No.: 13/504,943

(22) PCT Filed: Oct. 27, 2010

(86) PCT No.: PCT/US2010/054313
§ 371 (c)(1),
(2), (4) Date: Feb. 27, 2013

(87) PCT Pub. No.: WO2011/056663
PCT Pub. Date: May 12, 2011

(65) Prior Publication Data
US 2013/0189373 A1    Jul. 25, 2013

Related U.S. Application Data

(60) Provisional application No. 61/255,620, filed on Oct. 28, 2009.

(51) Int. Cl.
*A61K 31/7064* (2006.01)
*A61K 31/407* (2006.01)

(52) U.S. Cl.
USPC ............ 514/233.5; 514/49; 514/415

(58) Field of Classification Search
USPC ...................................... 514/233.5
See application file for complete search history.

(56) References Cited

U.S. PATENT DOCUMENTS 6,413,944 B1 * 7/2002 Townsend et al. ............ 514/49
2009/0117125 A1 * 5/2009 Su et al. ................. 424/141.1

OTHER PUBLICATIONS

Bradner, W.T. "Mitomycin C: a clinical update" Cancer Treatment Reviews 2001, 27, 35-50.*
Kakadiya, R.; Dong, H.; Lee, P-C.; Kapuriya, N.; Zhang, X.; Chou, T-C.; Lee, T-C.; Kapuriya, K.; Shah, A.; Su, T-L. "Potent antitumor bifunctional DNA alkylating agents, synthesis and biological activities of 3a-aza-cyclopenta[a]indenes" Bioorg Med Chem 2009, 17, 5614-5626.*
Lee, P-C.; Kakadiya, R.; Su, T-L.; Lee, T-C. "Combination of Bifunctional Alkylating Agent and Arsenic Trioxide Synergistically Suppresses the Growth of Drug-Resistant Tumor Cells" Neoplasia, May 2010, 12 (5), 376-387.*

* cited by examiner

*Primary Examiner* — Sean Basquill
*Assistant Examiner* — Andrew S Rosenthal
(74) *Attorney, Agent, or Firm* — VLP Law Group LLP; Kent H Cheng

(57) ABSTRACT

A pharmaceutical composition for treating cancer, in particular drug resistant cancer, comprising an effective amount of bifunctional alkylating agent, an effective amount of a DNA repair inhibitor, and a pharmaceutically acceptable carrier.

14 Claims, 20 Drawing Sheets

| TUMOR WEIGHT (g) | 2.44 ±0.26 | 2.32 ±0.37 | 1.36* ±0.18 | 0.62* ±0.06 |
|---|---|---|---|---|
| | CONTROL | ATO | BO-1012 | BO-1012 +ATO |

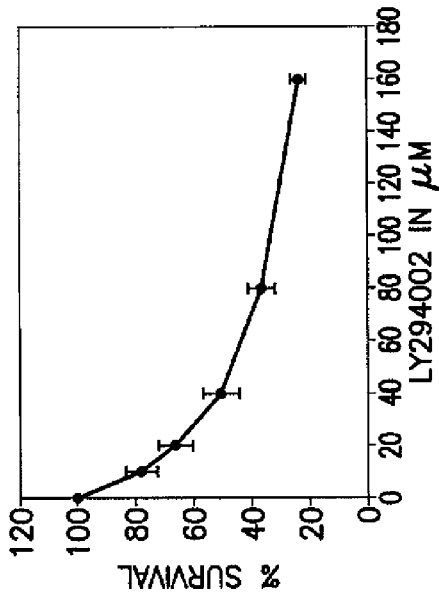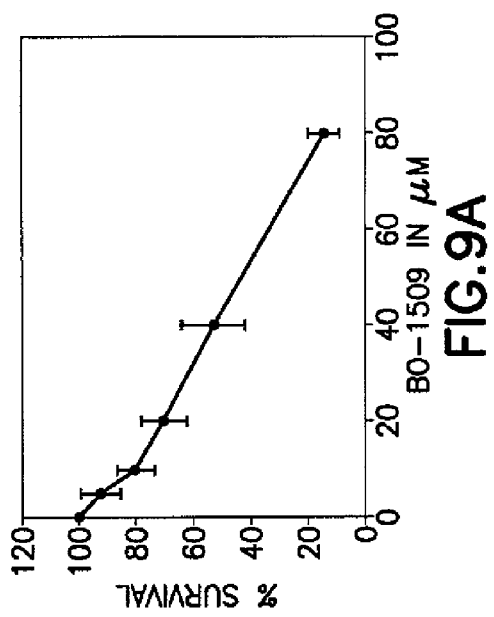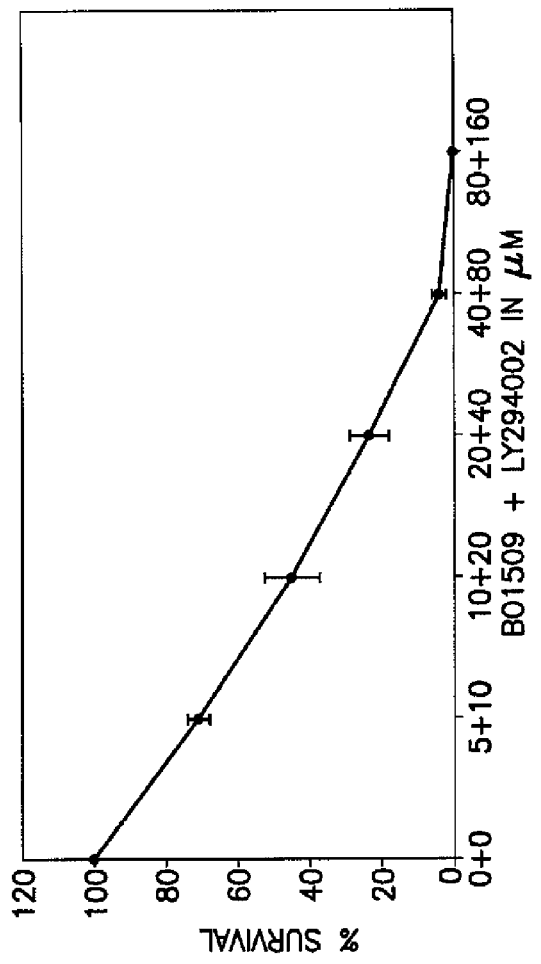

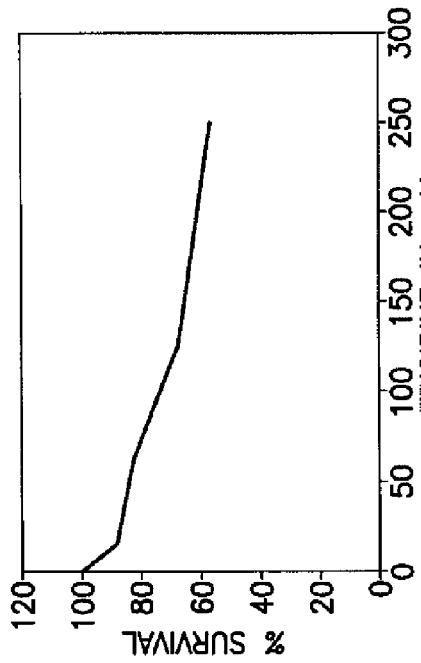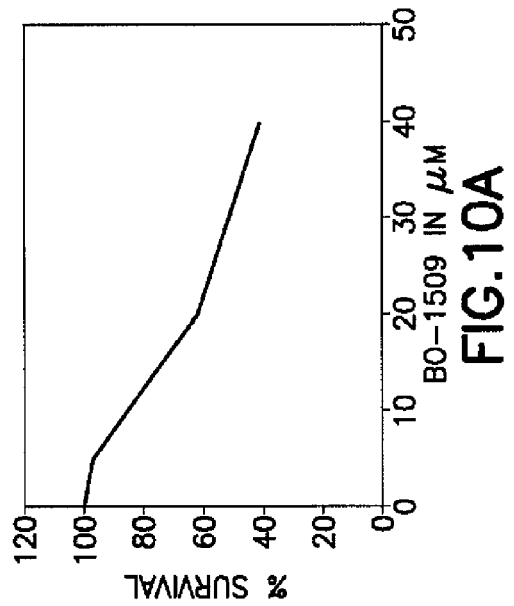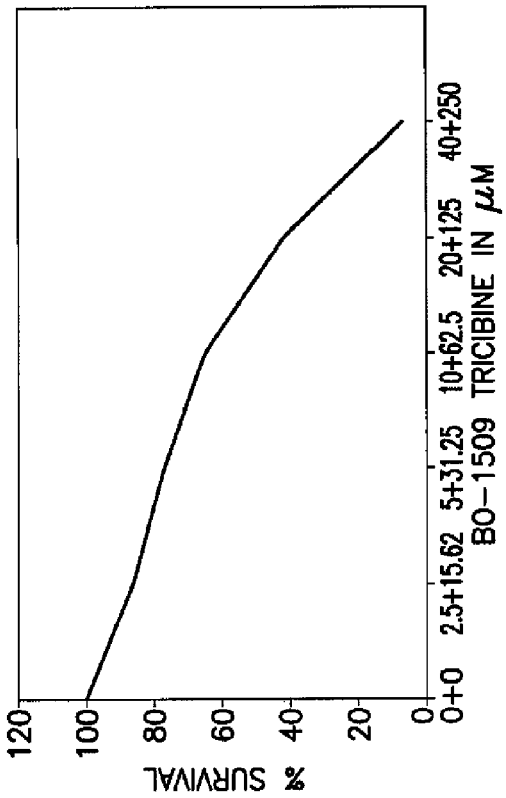
FIG. 10A
FIG. 10B
FIG. 10C

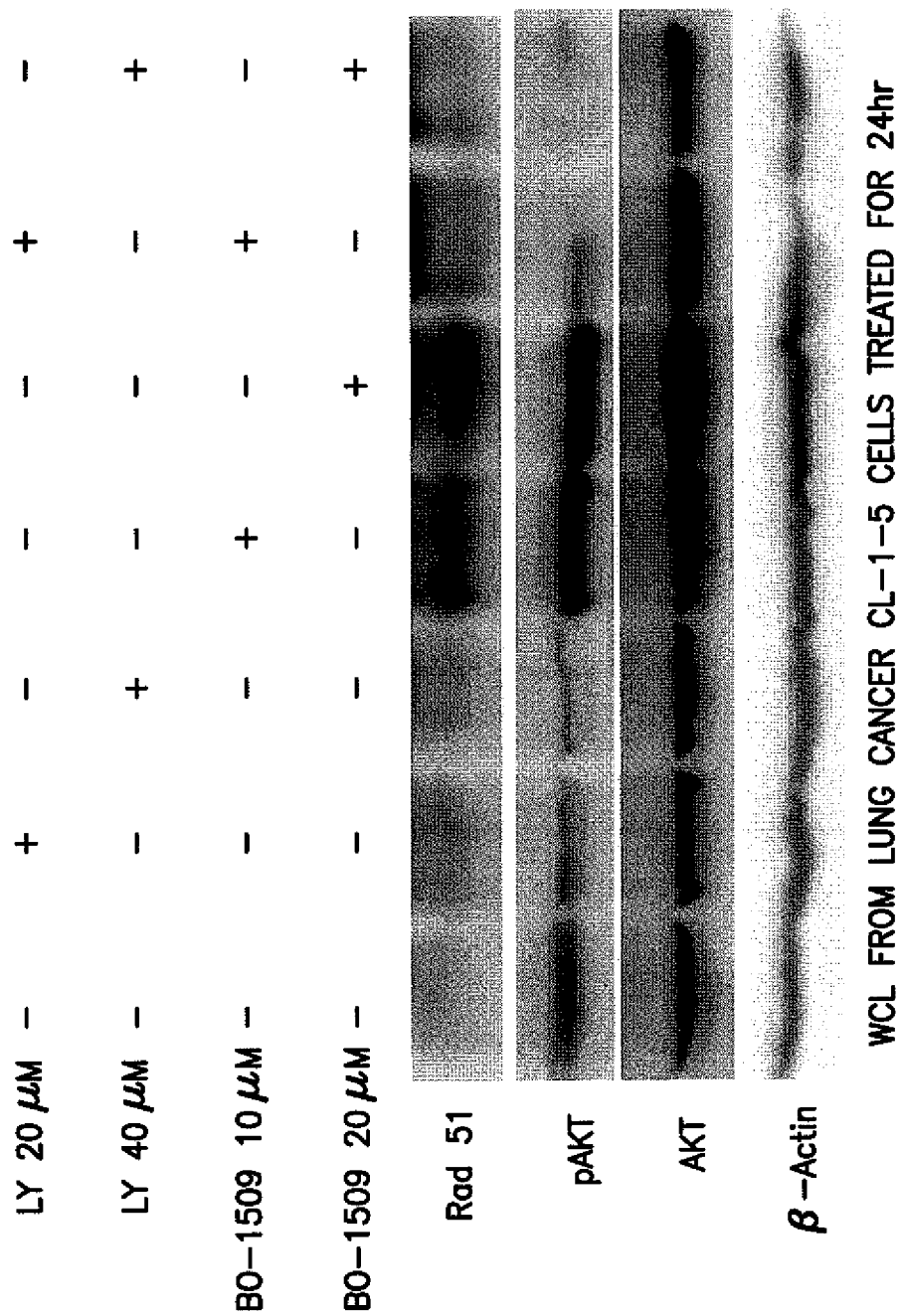

METHOD OF TREATING CANCER USING COMBINATION OF A BIFUNCTIONAL ALKYLATING AGENT AND DNA REPAIR INHIBITORS

PRIORITY CLAIM

This is a U.S. national stage of application No. PCT/US2010/054313, filed on Oct. 27, 2010. Priority is claimed on that PCT application and on the following application: U.S. Provisional Patent Application Ser. No. 61/255,620, filed: Oct. 28, 2009.

BACKGROUND OF THE INVENTION

1. Field of the Invention

The present application relates to compositions comprising a combination of a bifunctional alkylating agent and DNA repair inhibitors and use of the compositions in treating cancer, in particular drug resistant cancer.

2. Description of the Related Arts

DNA alkylating agents, commonly used as chemotherapeutic drugs for treatment of a variety of pediatric and adult cancers [1], exert their cytotoxic effects by directly interacting with DNA in a way that leads to DNA lesions. There are two types of DNA alkylating agents, monofunctional and bifunctional. Mechlorethamine, a bifunctional nitrogen mustard alkylating agent, was the first antitumor drug introduced into clinical practice more than 50 years ago [2]. Currently, a variety of bifunctional alkylating agents, such as the nitrogen mustards (e.g., melphalan [3]), nitrosoureas (e.g., carmustine [4]), alkyl sulfonates (e.g., busulfan [5]), aziridines (e.g., thiotepa [6]), platinum drugs (e.g., cisplatin [7]), and the natural product mitomycin C (MMC) [8], are still widely used for treatment of patients with malignant diseases. Although monofunctional alkylating agents mainly form genotoxic monoadducts to further induce mutagenic and carcinogenic DNA lesions, bifunctional alkylating agents form monoadducts, intrastrand crosslinks, and interstrand crosslinks (ICLs) on DNA, and also form DNA-protein crosslinks [9]. ICLs cause replisome dissociation and collapse, and subsequently induce DNA double-strand breaks (DSBs) (9, 10). The induction of ICLs by bifunctional alkylating agents therefore disturbs cell cycle progression and triggers cell death. Because the repair of ICLs is a laborious challenge as compared with other DNA damages, the formation of ICLs is the critical step in the cytotoxicity of bifunctional alkylating agents, and is recognized as a critical event in targeting cancer therapies [10,11]. Based on MMC and bis(carbamates)pyrrolizidines, we previously synthesized a series of bifunctional alkylating agents, bis(hydroxymethyl) of 3a-azacyclopenta[a]indene-1-yl, and their bis(methylcarbamate) derivatives (See figure below), and showed potent anticancer activity in a variety of in vitro cell models and in vivo xenograft mouse models [12]. It should be noted that we have filed a disclosure of these bifunctional alkylating agents in a U.S. provisional patent 61/255,620, filed Oct. 28, 2009. Among the series of derivatives of 3a-aza-cyclopenta[a]indenes, BO-1012 and BO-1509 induced a significant level of ICLs and suppressed the growth of human breast carcinoma cells transplanted in nude mice [12].

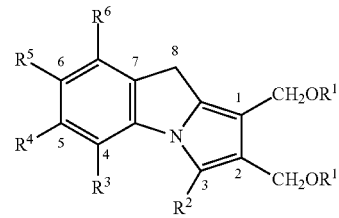

FIG. 1

Wherein
$R^1$ is H or chosen from a saturated or unsaturated, linear or branched, C1-C5 alkyl group, an optionally substituted phenyl group, and an optionally substituted benzyl group. $R^2$ is chosen from hydrogen, a C1-C5 linear or branched alkyl group, and aryl, a heteroaryl, and a benzyl, which may be unsubstituted or substituted; and $R^3$, $R^4$, $R^5$ and $R^6$ are independently chosen from hydrogen, C1-C6 alkyl, ORa, halo, cyano, nitro, $NH_2$, NHRb, $N(Rb)_2$, a C3-C6 cyclic alkylamino group or a methylenedioxy and ethylenedioxy group; wherein Ra is chosen from hydrogen and C1-C10 alkyl, and Rb is chosen from hydrogen and C1-C10 alkyl.

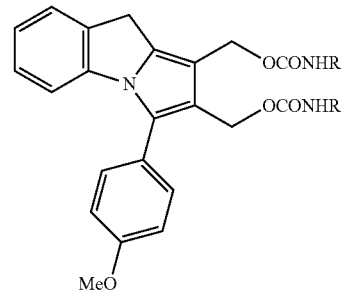

BO-1012 R = Me
BO-1509 R = Et

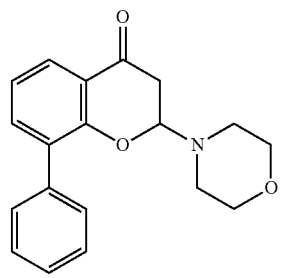

LY294002

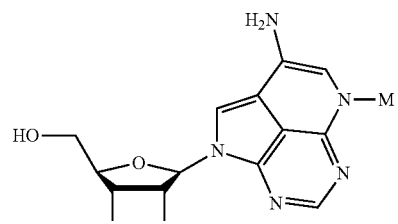

Triciribine

Among DNA repair inhibitors, arsenic trioxide (ATO) is an antineoplastic chemotherapeutic agent approved for treatment of relapsed or refractory acute promyelocytic leukemia (APL) [13]. ATO has also been reported to reduce cell viability, induce apoptosis, and inhibit tumor growth in myeloma cells at concentrations low enough for safe use in patients

[14]. Recent studies have further demonstrated that ATO is highly effective for triggering apoptosis in vitro in a variety of solid tumor cells and for inhibiting tumor growth in xenograft animal models [15]. The promising preclinical activity of ATO against solid tumors supports further investigation of clinical applications for ATO. However, preliminary reports from phase II clinical trials on patients with metastatic renal cell carcinoma [16], and metastatic melanoma [17] suggest that ATO used as a single therapeutic agent may have limited efficacy against solid tumors.

Alternatively, numerous reports have shown that ATO can be used in combination with agents that induce apoptosis [18-20], reduce glutathione [19], inhibit DNA methylation [21], or induce DNA damage [22]. ATO also enhances radiosensitivity to human cervical carcinoma and malignant glioma cells in vitro and in vivo by enhancing autophagic effects and preventing tumor invasion [22-26]. Moreover, a phase II trial of ATO in combination with melphalan and ascorbic acid against myeloma showed that the addition of ATO and ascorbic acid to high-dose melphalan is safe and well tolerated in patients with relapsed or refractory multiple myeloma [24].

Our early studies and others have reported antitumor effects of arsenic compounds on various tumor models [22, 25-27]. Numerous studies have shown that arsenic inhibits activity of proteins involved in DNA repair by various mechanisms [28,29], and interferes with both base excision repair and nucleotide excision repair [30]. Qian et al studied arsenic trioxide in the treatment of advanced primary liver and gallbladder cancer [27].

Another DNA repair inhibitor, LY294002 (FIG. 1, a flavonoid derivative) was reported to be able to inhibit DNA repair PI3K or PI3/Akt pathway and possessed antiproliferative and proapoptoic activity in vitro [31]. It was also shown that this agent inhibited tumor growth and induce apoptosis in human tumor cancer xenograft [32,33]. Another AKT inhibitor, triciribine (TCN, nucleoside analogue), was originally found to be a DNA synthesis inhibitor. This nucleoside has been implicated in many human cancers, including prostate carcinomas [34].

Because drug resistance, both inherited and acquired, is a pervasive problem and is a key factor contributing to the failure of clinical chemotherapy, it is of vital importance to develop a regime against cancers that are resistant to DNA damaging agents.

SUMMARY OF THE INVENTION

The present invention in one embodiment provides a pharmaceutical composition for treating cancer comprising an effective amount of bifunctional alkylating agent, an effective amount of a DNA repair inhibitor, and a pharmaceutically acceptable carrier. The bifunctional alkylating agent is preferably a derivative of 3a-aza-cyclopenta[a]indenes, such as BO-1012 or BO-1509. The DNA repair inhibitor is preferably arsenic trioxide, LY294002, or triciribine.

The present invention in another embodiment provides a method of treating cancer suffered by a mammalian subject comprising administering to the subject an effective amount of bifunctional alkylating agent and an effective amount of a DNA repair inhibitor. The subject may be administered with the bifunctional alkylating agent before being administered with the DNA repair inhibitor or in the opposite order, or may be administered simultaneously.

The bifunctional alkylating agent used in the method is preferably a derivative of 3a-aza-cyclopenta[a]indenes, such as BO-1012 or BO-1509. The DNA repair inhibitor used in the method is preferably ATO, Ly294002, or triciribine. The cancer that is to be treated by the method of the present invention may be one that is resistant to an individual therapeutic agent. The cancer may be one of the following: human lung cancer; human bladder cancer; human breast cancer; human prostate cancer; human glioma cancer; and human oral cancer.

I. Combination of BO-1012 with ATO

Inherited or acquired resistance to therapeutic agents is a crucial factor in the failure of cancer chemotherapy. In this study, we explored the effect of combining a synthetic bifunctional alkylating agent, BO-1012 with arsenic trioxide (ATO) on cytotoxicity in human lung cancer H460 cells, which are more resistant to BO-1012 and ATO than several other cancer cell lines used. Our results showed a synergistic enhancement of cytotoxic effects by treatment of H460 cells with BO-1012 for 1 h followed by ATO for 72 h as compared to treatment with either agent alone. A modified comet assay indicated that the repair of BO-1012-induced DNA interstrand crosslinks was significantly inhibited by ATO. Consequently, a protein marker for DNA double-strand breaks, γH2AX, was remarkably increased and formed nuclear foci in H460 cells treated with this drug combination. Combined treatment also resulted in severe G2/M arrest and apoptosis. In a xenograft mouse model, we demonstrated that combination treatment with BO-1012 and ATO synergistically reduced tumor volumes in nude mice inoculated with H460 cells. Similarly, the combination of BO-1012 and ATO effectively reduced the growth of cisplatin-resistant NTUB1/P human bladder carcinoma cells. These results reveal that a combination of bifunctional alkylating agents and ATO may be a rational strategy for treating cancers with inherited or acquired drug resistance.

II. Combination of BO-1509 with LY294002 and Triciribine

Moreover, we recently found that combination of BO-1509 (another derivative of 3a-aza-cyclopenta[a]indene) and LY294002 or triciribine synergistically killed human lung adenocarcinoma CL-1-5 in culture. The values of CI were ranged from 0.132 to 0.953 at the doses used for combination of BO-1509 and LY294002 and 0.175 to 0.643 for that of BO-1509 and triciribine. In CL-1-5 xenograft animal model, the combination of BO-1509 and LY294002 or tribune significantly suppressed the tumor growth. The present results revealed that combination of 3a-aza-cyclopenta[a]indenes and DNA repair inhibitor is able to effectively inhibit the inherited or acquired drug-resistant cancers.

BRIEF DESCRIPTION OF THE DRAWINGS

FIG. 1 shows enhanced cytotoxicity of BO-1012 by ATO in human cancer cell lines.

H460, H1299, and PC3 cells were co-treated with both BO-1012 and ATO for 72 h. Cell viability was assessed and the $IC_{50}$ values of BO-1012 in combination with or without ATO treatment were calculated. *, $p<0.05$ as compared to BO-1012 treatment alone in each cell line.

Figure 3A:
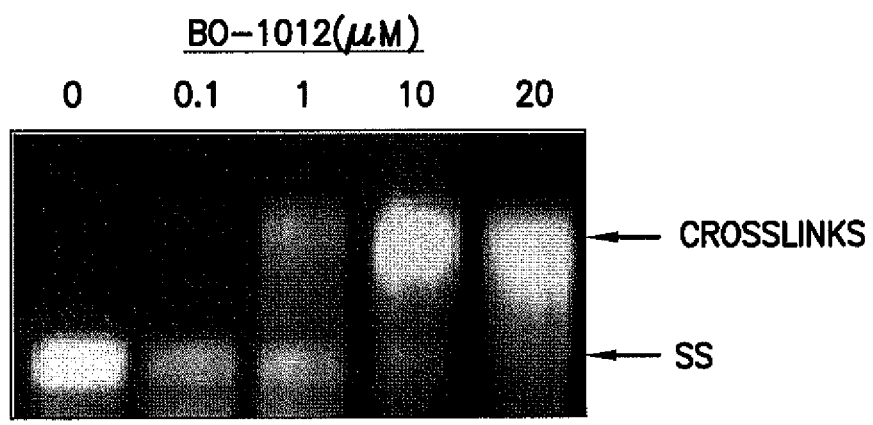
Figure 3B:
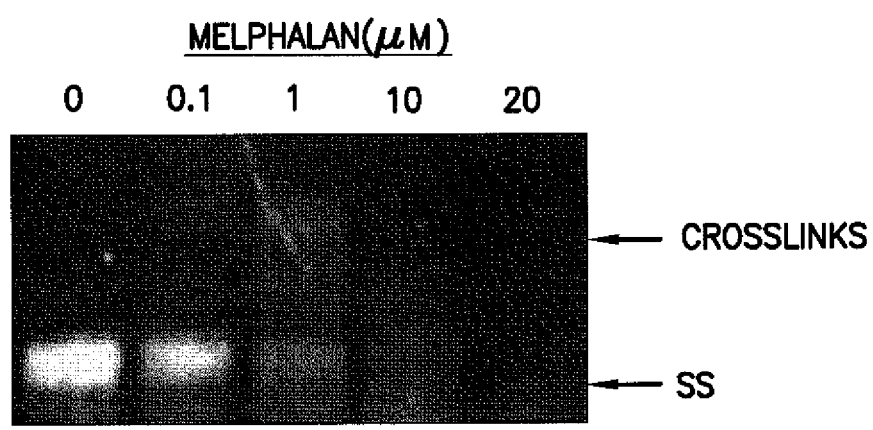
Figure 3C:
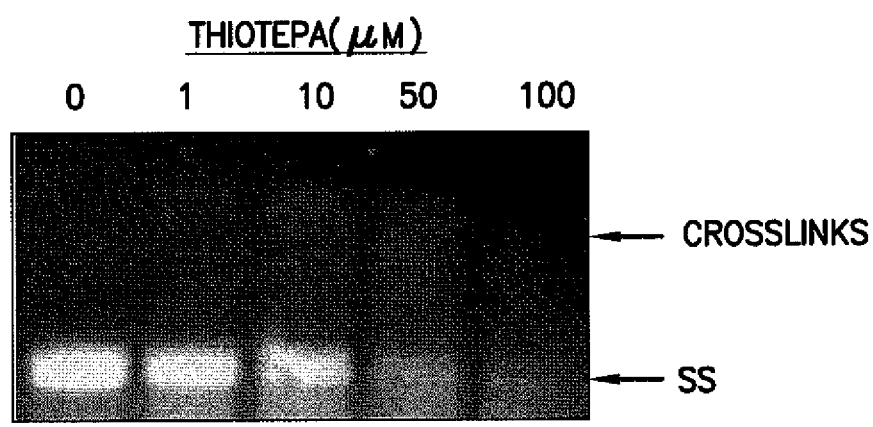

FIG. 3 shows formation of DNA ICLs by BO-1012, melphalan, and thiotepa. pEGFP-N1 plasmid DNA was incubated with various concentrations of drugs. At the end of treatment, the DNA ICLs were analyzed by alkaline gel shift assay as described in Materials and Methods. ss, single-strand DNA; Crosslinks, DNA ICLs.

Figures 4A, 4B:
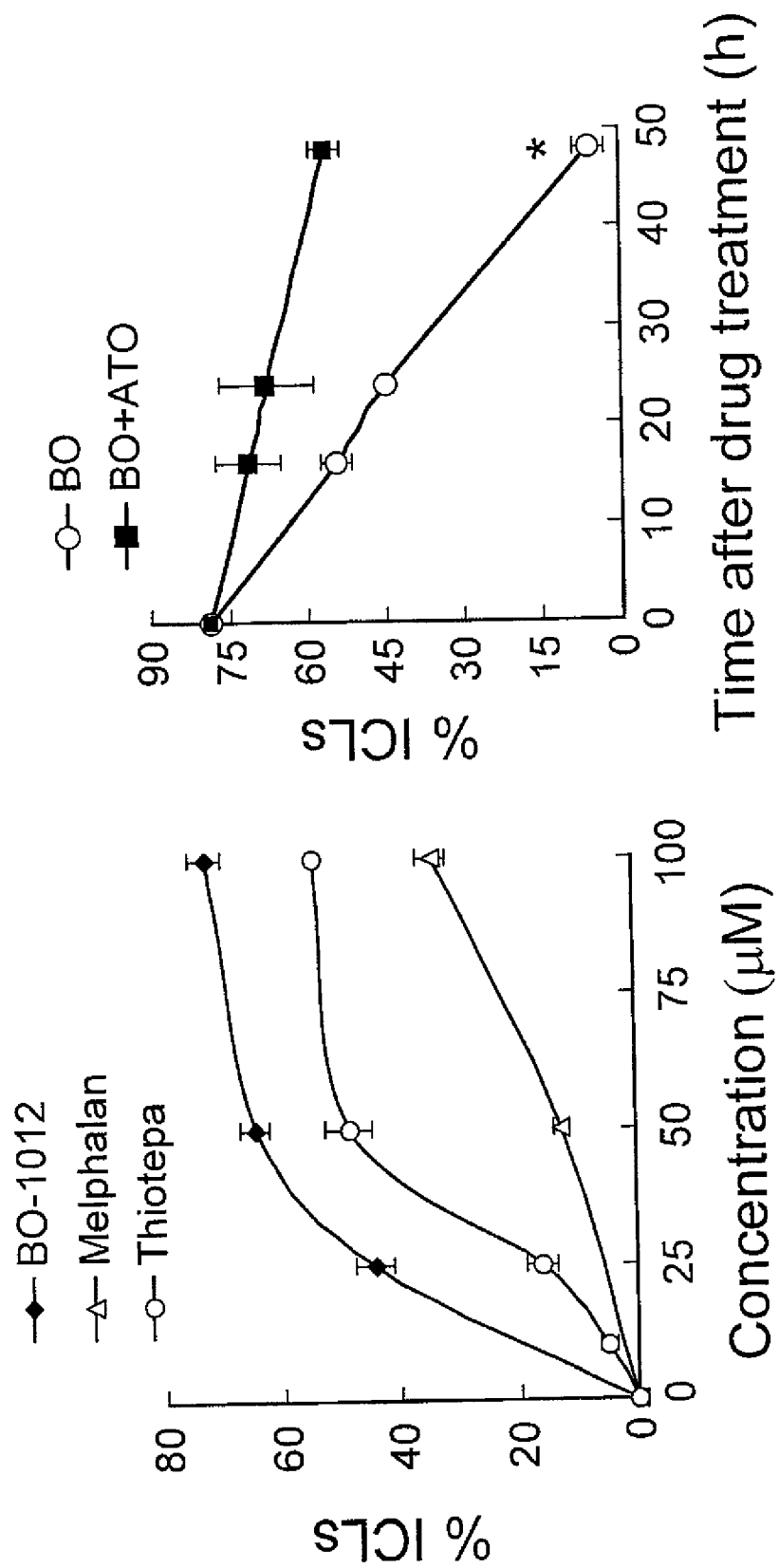
Figure 4C:
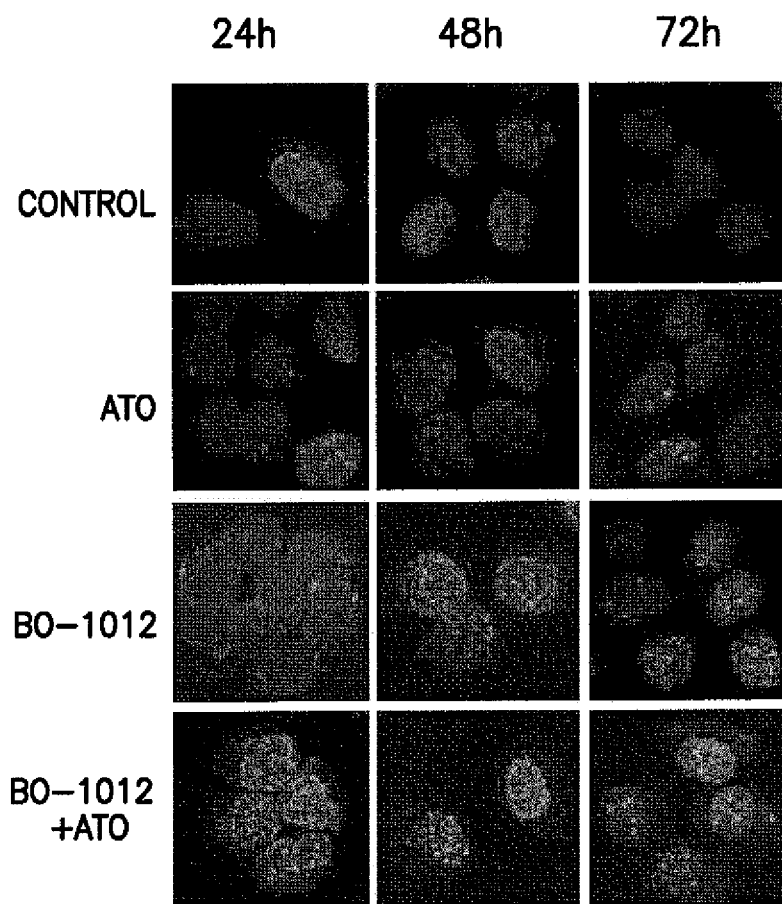
Figure 4D:
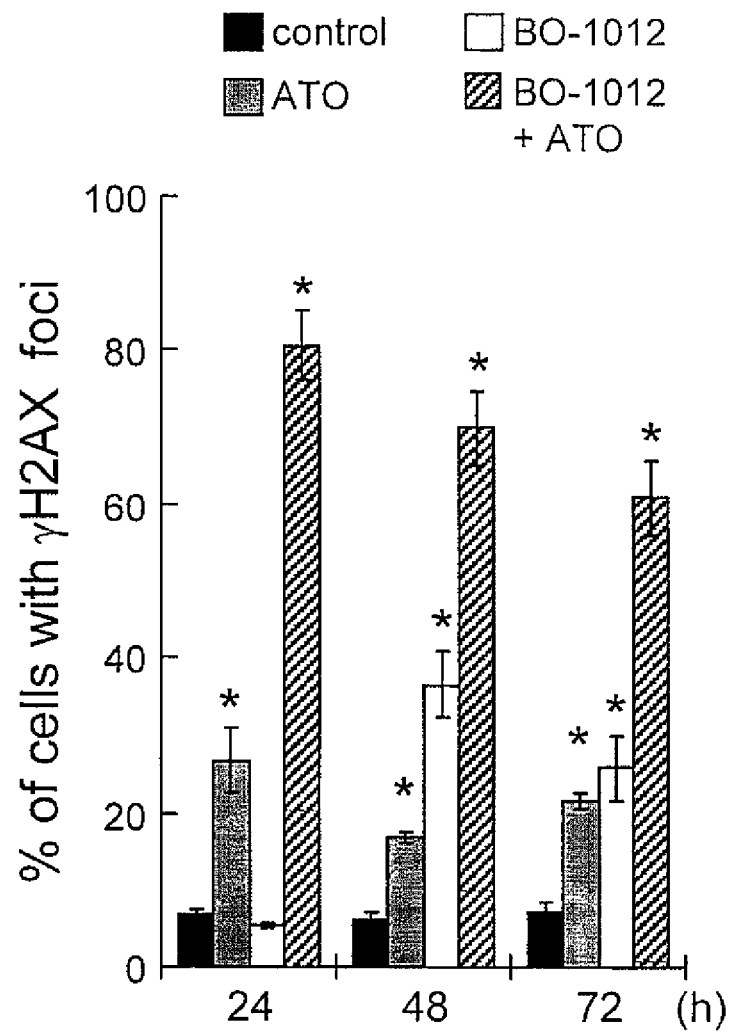

FIG. 4 shows inhibition of the repair of BO-1012-induced DNA damage and exaggeration of DSB formation by ATO. FIG. 4A shows induction of ICLs by BO-1012, melphalan, and thiotepa. H460 cells were treated with various concentrations of BO-1012, melphalan, or thiotepa for 1 h and then subjected to the modified comet assay as described in Materials and Methods. Percentage of DNA ICLs was calculated by the percentage of decrease in tail moment. FIG. 4B shows inhibition of the repair of BO-1012-induced DNA ICLs by ATO. H460 cells were treated with 40 μM BO-1012 for 1 h, washed, and then treated with 8 μM ATO for 16, 24, and 48 h. *, $p<0.05$ as compared to BO-1012 alone at the indicated time. FIG. 4C shows enhanced formation of BO-1012-induced γH2AX nuclear foci by ATO. H460 cells were treated with BO-1012 and ATO, alone or in combination, as described above. After treatment, the detection of γH2AX (green) immunofluorescence staining was performed as described in Materials and Methods. Nuclei were stained by DAPI (blue). FIG. 4D shows the percentage of cells containing ≥4 γH2AX nuclear foci determined under a fluorescence microscope. *, $p<0.05$ as compared to the control at each time point.

Figure 5:
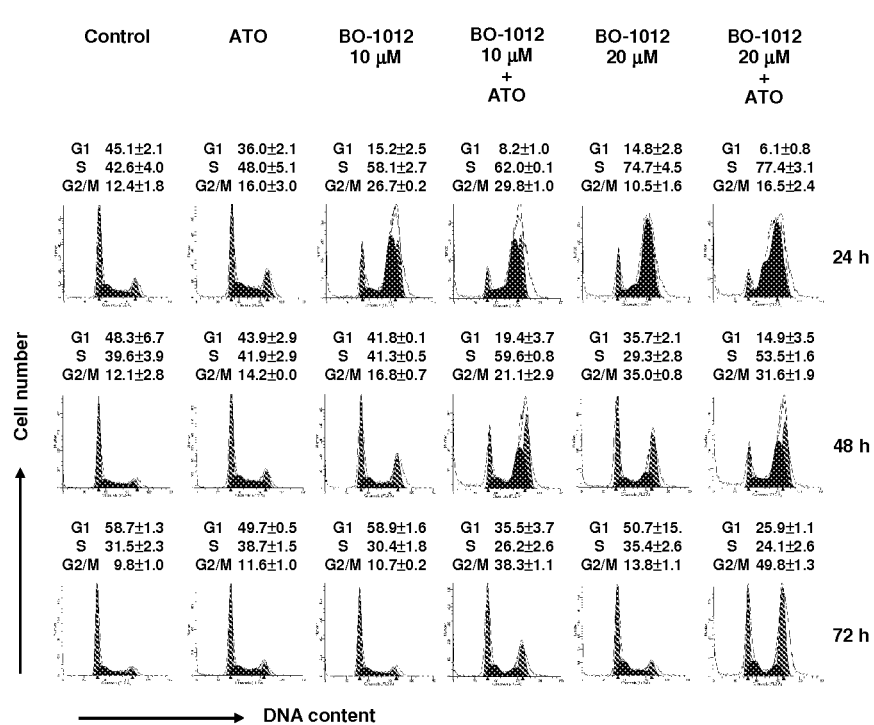

FIG. 5 shows cell cycle perturbation induced by BO-1012 and ATO, alone or in combination. H460 cells were treated with 10 or 20 μM BO-1012 for 1 h, washed, and then treated with 8 μM ATO for 24, 48, or 72 h. After treatment, cell cycle analysis was performed by flow cytometry as described in Materials and Methods. Representative DNA histograms of three independent experiments with similar results are shown. Cell cycle distribution was shown at the top of each histogram.

Figure 6:
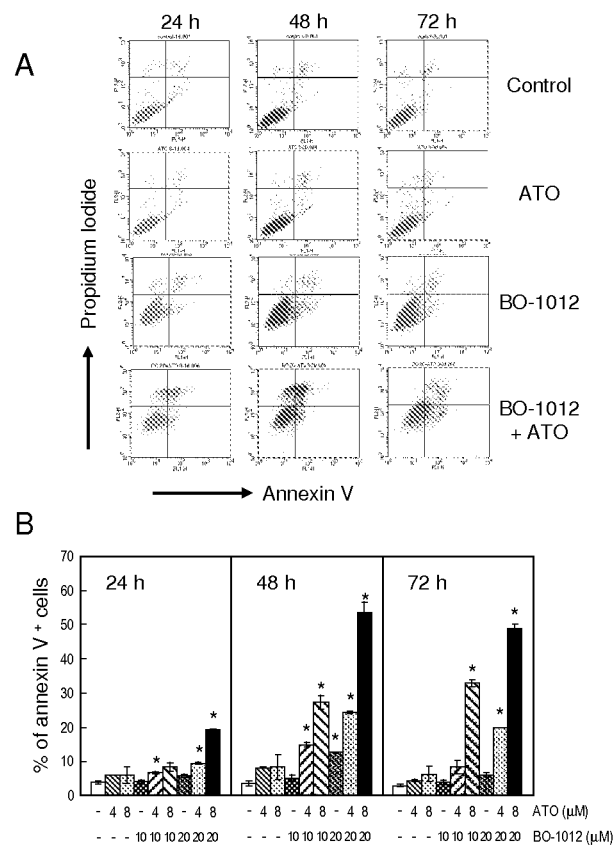

FIG. 6 shows apoptotic cell death induced by BO-1012 and ATO, alone and in combination.

H460 cells were treated with 10 or 20 μM BO-1012 for 1 h, washed, and then treated with 4 or 8 μM ATO for 24, 48, or 72 h. After treatment, the cultures were analyzed for apoptosis using annexin V staining. FIG. 6A shows representative flow cytometric analysis of apoptotic cell death. H460 cells were treated with 20 μM BO-1012 for 1 h and then treated with 8 μM ATO for 24, 48, or 72 h. FIG. 6B shows percentage of annexin $V^+$ cells (top and bottom right quadrants). *, $p<0.05$ as compared to the control at each time point.

FIG. 7 shows synergistic anticancer activity of combined ATO and BO-1012 on H460 xenografts. Nude mice with H460 xenografts were injected i.v. daily with 5 mg/kg ATO, 2.5 mg/kg BO-1012, or a combination of both agents for 5 days (indicated by arrows). FIG. 7A shows tumor volumes measured with calipers every 2 or 3 days. Six to seven animals were in each group. FIG. 7B shows representative images of mice bearing tumors at day 23. The average tumor weights are shown at the bottom. *, $p<0.05$ as compared to the control. FIG. 7C shows change in mouse body weight. The body weights were measured every 2 or 3 days. FIG. 7D shows PCNA immunohistochemistry and TUNEL assay. One day after the last treatment (i.e., day 6), xenograft tumor sections were taken from each group, sectioned, and subjected to PCNA immunohistochemistry and TUNEL assay as described in Materials and Methods.

FIG. 8 shows synergistic anticancer activity of combined ATO and BO-1012 on human bladder cancer cells (NTUB1) and derived cisplatin-resistant (NTUB1/P) cells. FIGS. 8A and 8B show cell viability analysis of BO-1012 and ATO, alone and in combination, in NTUB1 (A) and NTUB1/P (B) cells. Cell viability was assayed as described in FIG. 1A. *, $p<0.05$ as compared to ATO alone at each concentration. FIGS. 8C and 8D show anticancer activity of BO-1012 and ATO, alone and in combination, against NTUB1 (C) and NTUB1/P (D) tumors. Mice bearing NTUB1 or NTUB1/P xenografts were treated as described in FIG. 7A. Four to six animals were in each group. The tumor volumes were measured with calipers at the indicated times.

FIG. 9 shows the synergistic cytotoxicity of BO-1509 and LY294002 (PI3K inhibitor) to human lung adenocarcinoma CL-1-5.

Figure 9D:
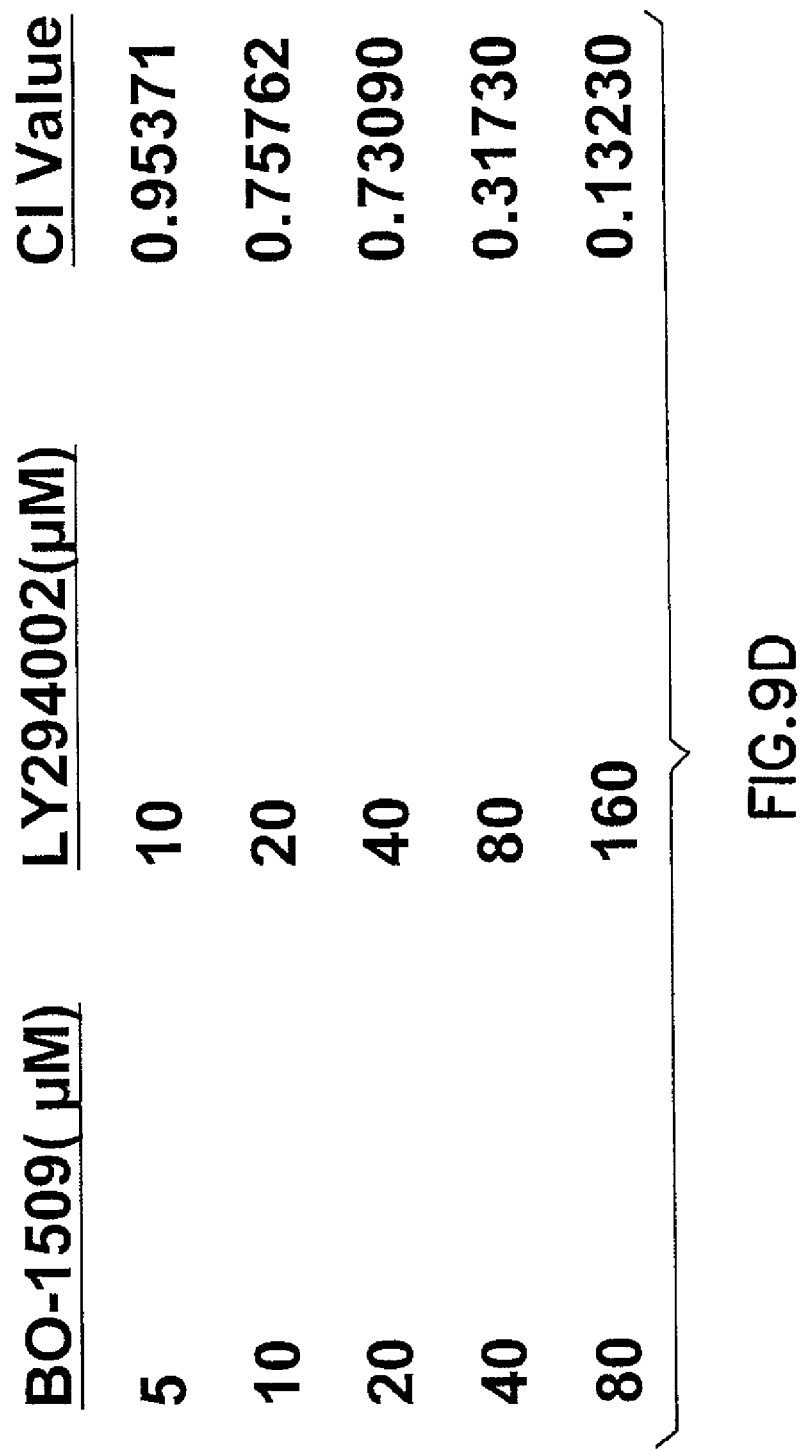

CL-1-5 cells were plated on 96-well plates at the cell density of 3,000 cells per well. After overnight incubation, the cells were treated with various concentrations of BO-1509 or LY294002, or in combination for 72 h. The cell number was determined by Almar blue assay. FIGS. 9A and 9B shows the survival curves of CL-1-5 treated with BO-1509 and LY294002, respectively. FIG. 9C shows the survival curve of CL-1-5 treated with in combination of BO-1509 and LY294002 at the ratio of 1:2. FIG. 9D shows the CI values calculated according to the equation developed by Chou and Thalay.

FIG. 10 shows the synergistic cytotoxicity of BO-1509 and triciribine (AKT inhibitor) to human lung adenocarcinoma CL-1-5.

Figure 10D:
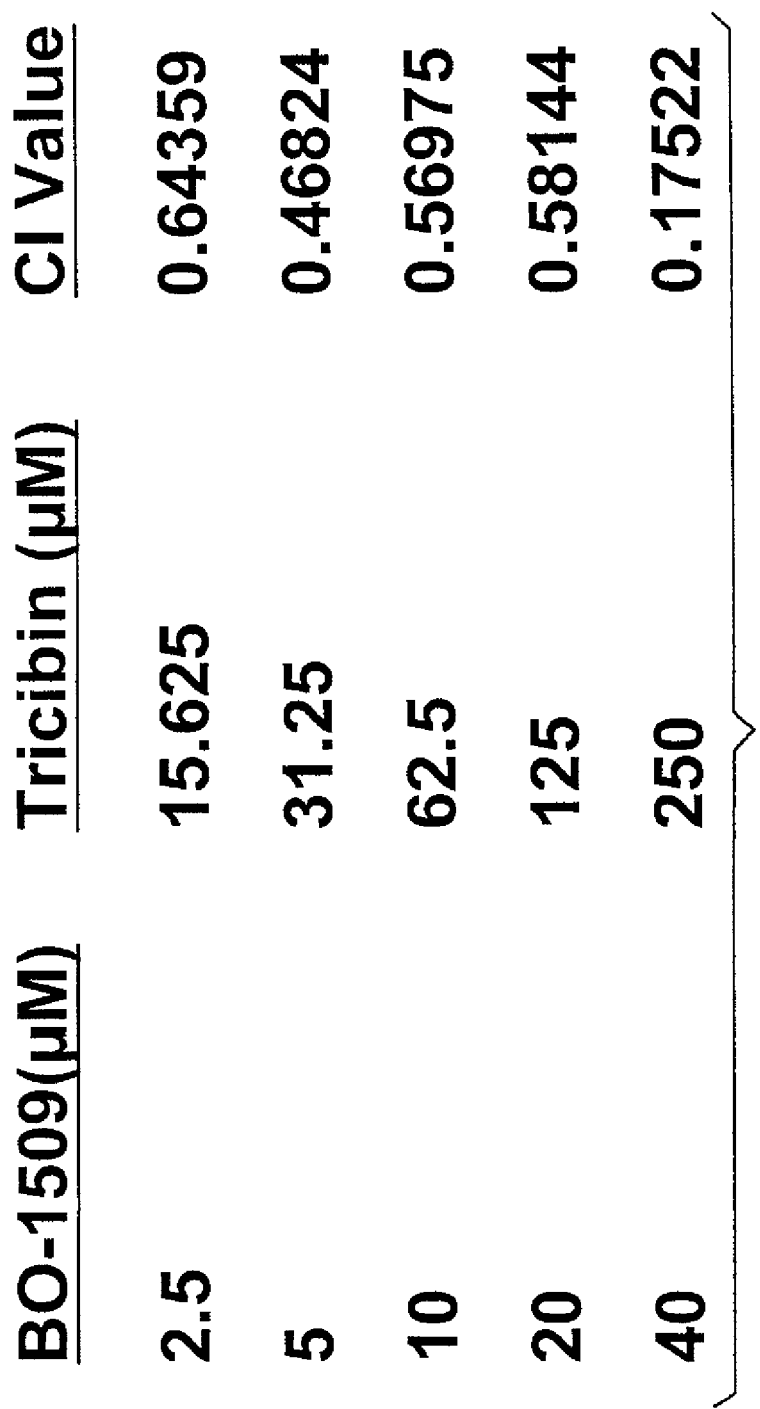

As described in FIG. 9, FIGS. 10A and 10B shows the survival curves of CL-1-5 treated with BO-1509 and triciribine, respectively. FIG. 10C shows the survival curve of CL-1-5 treated with in combination of BO-1509 and triciribine at the ratio of 1:6.25. FIG. 10D shows the CI values calculated according to the equation developed by Chou and Thalay.

FIG. 11 shows the abrogation of BO-1509-activated AKT and Rad51 by LY294002 in CL-1-5 cells.

Logarithmically growing CL-1-5 cells were treated with BO-1509 (10 or 20 μM) and LY294002 (20 and 40 μM), either alone or in combination, for 24 h. At the end of treatment, the whole cell lysates were harvested. The protein levels of AKT, pAKT, and Rad51 were determined by Western blotting assay. β-actin was used as loading control. FIG. 11 shows BO-1509 could activate the AKT to form pAKT and enhance the expression of Rad51, an essential component of homologous recombination repair (lanes 4 and 5). Combined treatment with BO-1509 and LY294002 not only suppresses the activation of AKT, but also inhibits the synthesis of Rad51 (lanes 6 and 7).

FIG. 12 shows synergistic anticancer activity of combined BO-1509 and DNA repair inhibitor (LY294002 or triciribine) on CL-1-5 xenografts.

An aliquot of 10 million CL-1-5 cells was injected to 6 week old male nude mice. At 8th day when tumors were about 200 mm³, the mice with CL-1-5 xenografts were divided into 6 groups (n=3 for each group). Group 1 were injected i.v. with vehicle only, group 2 BO-1509 at 10 mg/Kg (Q2D×5), group 3 LY294002 at 40 mg/Kg (QD×9), group 4 AKTi (triciribine) at 1 mg/Kg (Q2D×5), group 5 BO-1509 plus AKTi (QD×5), and group 6 BO-1509 (Q2D×5) plus LY294002 (QD×9).

Figure 12A:
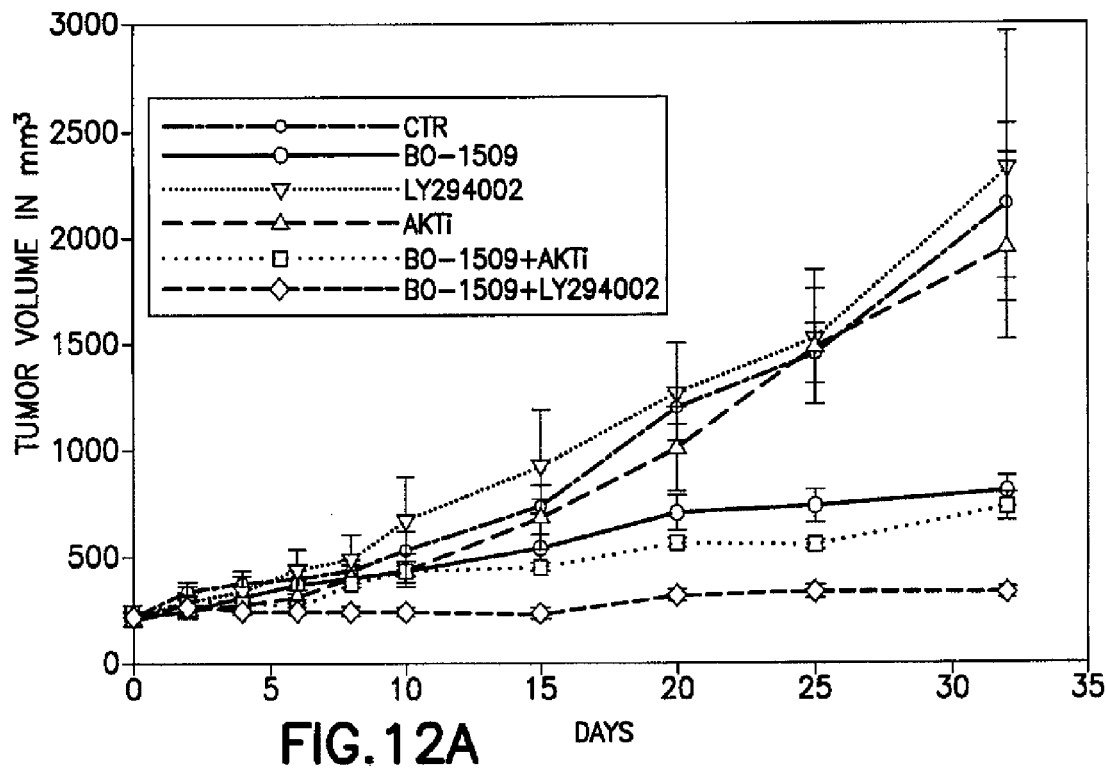
Figure 12B:
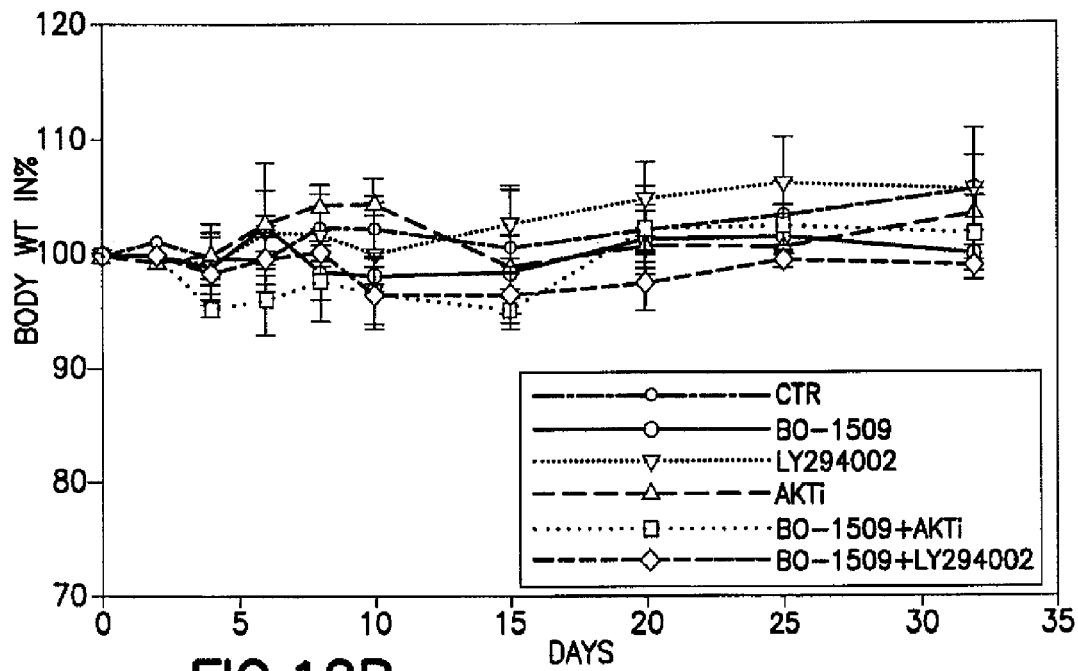

FIG. 12A shows tumor volumes measured with calipers every 2 or 3 days. FIG. 12B shows no significant change in mouse body weight.

DETAILED DESCRIPTION OF THE PRESENTLY PREFERRED EMBODIMENTS

The following examples are provided for the purpose of further illustration only and are not intended to be limitations on the disclosed invention.

Materials and Methods

Reagents and Chemicals. BO-1012 and BO-1509 were synthesized in a four-step reaction as described previously [12]. Briefly, coupling of indole-2-carboxylic acid with 4-methoxybenzoyl chloride afforded 1-(4-methoxybenzoyl)-2,3-dihydro-1H-indole-2-carboxylic acid, which was converted to diester by reacting with dimethyl acetylenedicarboxylate in acetic acid. The diester was reduced by $LiAlH_4$/$CH_2Cl_2$, and followed by treating with methyl isocynate or ethylisocynate to afford the desired BO-1012 (methylcarbamic acid 3-(4-methoxy-phenyl)-2-methyl-carbamoyloxymethyl-8H-3a-aza-cyclopenta[a]inden-1-yl-methyl ester) and BO-1509 (ethylcarbamic acid 3-(4-methoxy-phenyl)-2-methyl-carbamoyloxyethyl-8H-3a-aza-cyclopenta[a]inden-1-yl-methyl ester), respectively, as an amorphous solid. The structures of BO-1012 and BO-1509 were confirmed by mass spectroscopy and by $^1H$ and $^{13}C$ nuclear magnetic resonance. ATO and other reagents were purchased from Merck (Darmstadt, Germany), LY294002 and triciribine (from Cayman Chemical, MI) and melphalan and thiotepa from Sigma-Aldrich (St. Louis, Mo.). Chemicals for cell culture were obtained from Gibco (Grand Island, N.Y.), and fetal bovine serum (FBS) from HyClone (Logan, Utah).

Cell Lines and Cell Culture. H460 (human lung large cell carcinoma cells), H1299 (human lung large cell carcinoma p53-deficient cells), PC3 (human prostate carcinoma cells), U87 (human glioma cells), and MCF7 (human breast carcinoma cells) were purchased from the American Type Culture Collection (Rockville, Md.). OEC-M1 (human gingival squamous cell carcinoma cells) was obtained from Dr. C.-L. Meng (National Defense Medical College, Taiwan) [36]. NTUB1 (human bladder transitional carcinoma cells) and the cisplatin-resistant sub-line NTUB1/P were provided by Dr. Y.-S. Pu (National Taiwan University Hospital, Taiwan) [37,38]. CL-1-5 (human lung adenocarcinoma cells) was obtained from Dr. P. C. Yang (National Taiwan University). All cell lines (except U87, which was grown in MEM medium) were cultured in RPMI1640 medium supplemented with 10% FBS and antibiotics, and incubated at 37° C. in a humidified atmosphere with 5% $CO_2$.

Measurement of Cell Viability. Cell viability was assessed using the cell proliferation reagent WST-1 (Roche Molecular Biochemicals, Penzberg, Germany), which is a tetrazolium salt that is cleaved by mitochondrial dehydrogenase in viable cells. In brief, 2,000-7,000 cells were seeded in each well of 96-well plates and incubated at 37° C. overnight prior to drug treatment. After a 72-h incubation with BO-1012 alone (0.1~80 µM), ATO alone (1~8 µM), or BO-1012 plus ATO, WST-1 solution was added to each well at a 1:10 dilution, and cells were incubated at 37° C. in 5% $CO_2$ for 4 h. Cell viability was assessed by absorbance at 460 nm using an automatic enzyme-linked immunosorbent assay (ELISA) plate reader. The $IC_{50}$ value for each drug, alone or in combination, was calculated using CompuSyn software (version 1.0.1; CompuSyn, Inc.). The interactions between ATO and BO-1012 were evaluated by the Chou-Talalay combination indices (CI) [39], where CI<1 indicates synergy; CI=1, additivity; and CI>1, antagonism.

Modified Single-Cell Gel Electrophoresis (Comet) and DNA ICL Repair Assays. The formation and the repair of DNA ICLs in H460 cells was analyzed using a modified comet assay as described previously [12].

Cell Cycle Analysis. H460 cells were treated with BO-1012 and ATO, separately or in combination, as described above. Cell cycle analysis was performed as described previously [40]. In brief, at the end of treatment, the attached cells were trypsinized, fixed with ice-cold 70% ethanol, and stained with 4 µg/ml propidium iodide (PI) in PBS containing 1% Triton X-100 and 0.1 mg/ml RNase A, and then subjected to flow cytometric analysis (FACScan flow cytometer, Becton Dickinson, San Jose, Calif.). The cell cycle phase distribution was analyzed using ModFit LT 2.0 software (Verity Software House, Topsham, Me.).

Measurement of Histone H2AX Phosphorylation. After treatment with BO-1012, ATO, or a combination of both agents for 24, 48, or 72 h, cells were fixed with 70% ethanol for 16 h, washed with PBS, and incubated with mouse anti-γH2AX antibody (Upstate) for 2 h, followed by FITC-conjugated goat anti-mouse (Jackson ImmunoResearch Laboratories, West Grove, Pa.) for 30 min. Cells were then stained in PBS containing 4 µg/mL PI and 0.1 mg/mL RNase A, and analyzed with a FACScan flow cytometer. γH2AX-labeled cells were gated according to control histograms and the percentage of them in a total 10,000 cells was calculated for each treatment.

Immunofluorescence Staining. H460 cells were cultured onto slides and then treated with BO-1012 and ATO, separately and in combination as described above, for 24, 48, or 72 h. To visualize γH2AX, cells were washed with cold PBS and fixed with 100% ice-cold methanol for 30 min. Slides were washed with PBS and incubated with anti-γH2AX antibody for 2 h at room temperature followed by Alexa Fluor 488-conjugated secondary antibodies (Molecular Probes, Eugene, Oreg.) and DAPI. After mounting with 50% glycerol, slides were subjected to confocal image analysis (Radiance 2100 System, Bio-Rad). Cells with at least four γH2AX foci in nuclei were counted as positive.

Apoptosis Assays. H460 cells were exposed to BO-1012, ATO, or a combination of both agents and then apoptosis was detected by flow cytometry using the Annexin V-FITC Apoptosis Detection Kit (Calbiochem, La Jolla, Calif.) according to the manufacturer's instructions. In the annexin V flow cytometry assay, the cells positive for annexin V staining only (bottom right quadrant) and positive for both annexin V and DNA staining (top right quadrant) represent the early and late apoptotic populations, respectively. The cells positive for DNA staining only (top left quadrant) represent the necrotic population.

Xenograft Mouse Model and Therapy. Animal care was approved by and followed the guidelines of the Academia Sinica Institutional Animal Care and Utilization Committee. Male Balb/c nude mice 6 weeks of age were obtained from the National Laboratory Animal Center (Taipei, Taiwan). The animals were housed in a specific pathogen-free (SPF) environment under controlled conditions of light and humidity, and were given sterilized food and water ad libitum. They were allowed to acclimate for 48 h after shipment before tumor inoculation was carried out. H460, NTUB1, or NTUB1/P cells in 50 µl of PBS, pH 7.4, were inoculated subcutaneously into the back of mice. When the resulting tumors reached 80-100 $mm^3$ in diameter, mice were randomly assigned to different treatment groups. ATO (5 mg/kg body weight), BO-1012 (2.5 mg/kg), or a combination with both agents was injected i.p., five times daily (QD×5). To monitor tumor formation, the longest and shortest diameters of the tumors were measured using calipers. Tumor volume (in mm$^3$) was calculated according to the following formula: tumor volume=(length×width$^2$)/2. Mouse body weight was also measured every 2-3 days and used as an indicator of the systemic toxicity of the treatment. For CL-1-5 xenograft model, we injected 10 million CL-1-5 cells subcutaneously into 6 week old male nude mice. At 8th day when tumors were about 200 mm$^3$, the mice were treated with BO-1509, LY294002 and triciribine, either alone or in combination, according to the protocol as indicated. Tumor volumes and mouse body weight were monitored as described above.

Terminal Deoxynucleotidyl Transferase-Mediated dUTP Nick End Labeling (TUNEL) Assay. The TUNEL assay was performed to quantify apoptotic cells in xenograft tumor sections using the Dead End kit (Promega, Madison, Wis.) with the assistance of an autostainer (Dako, Carpinteria, Calif.). The assay was carried out according to the manufacturer's instructions.

Immunohistochemical Staining. Immunohistochemical analysis of proliferating cell nuclear antigen (PCNA) was conducted on established tumors from mice 1 day after treatment. One day after the last injection with drugs (day 6), three mice from each group were sacrificed and tumors were sectioned and then stained with anti-PCNA antibody (PC-10, mouse IgG, DakoCytomation, Carpinteria, Calif.). The standard immunohistochemical staining was then performed according to the manufacturer's instructions of LSAB2 streptavidin-biotin complex system (Dako Corp.).

Statistical Analysis. All data represent at least three independent experiments. The data are presented as means±SE. The statistical significance of differences was assessed using the Student's t-test.

Results

Figure 1A:
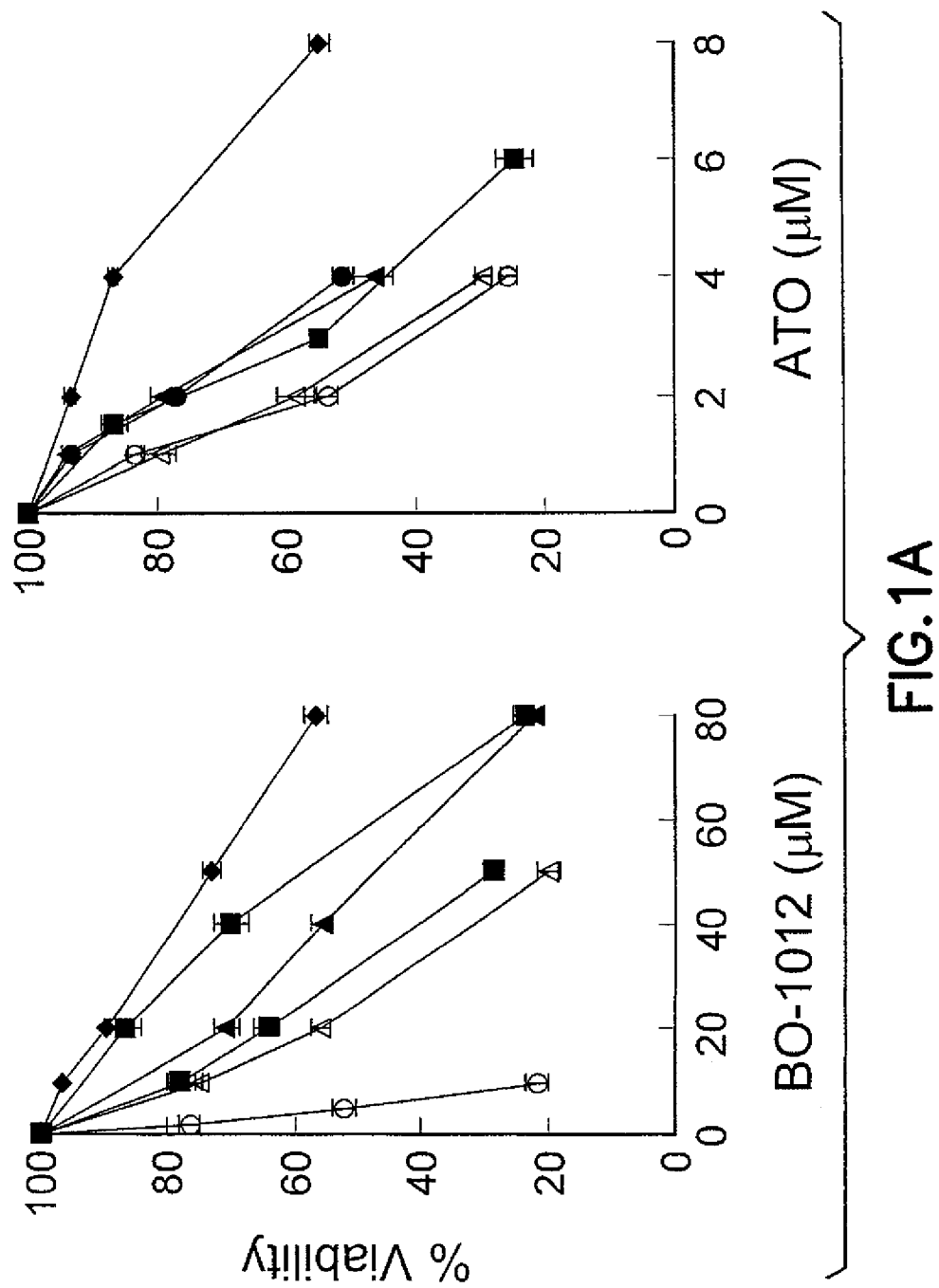
FIG. 1A shows cytotoxicity of human cancer cell lines to BO-1012 and ATO. Six human cancer cell lines (H460, H1299, PC3, U87, MCF7, and OECM1) were treated with various concentrations of BO-1012 or ATO for 72 h. Cell viability was determined by the WST-1 assay.

ATO Sensitizes Human Solid Tumor Cells to BO-1012. We recently reported that BO-1012 exhibits potent anticancer activity against human lymphoblastic leukemia and various solid tumors in vitro and against tumor xenografts in vivo [12]. In this study, we first investigated whether ATO could sensitize human solid tumor cell lines to BO-1012-induced cell death. Six tumor cell lines (H460, H1299, PC3, U87, MCF7, and OEC-M1) were treated with various concentrations of BO-1012 (0.1~80 μM), or ATO (1~8 μM) for 72 h. The inhibitory effect of BO-1012 against these tumor cell lines covered a wide range, with IC$_{50}$ values ranging from 5.2 μM (OEC-M1 cells) to 63.8 μM (H460 cells). OEC-M1 and MCF7 cells were highly susceptible to BO-1012, whereas H460 and H1299 cells were more resistant (FIG. 1A). Similarly, ATO was significantly more cytotoxic to OECM1 and MCF7 cells than to H460 cells (FIG. 1A).

Figure 2:
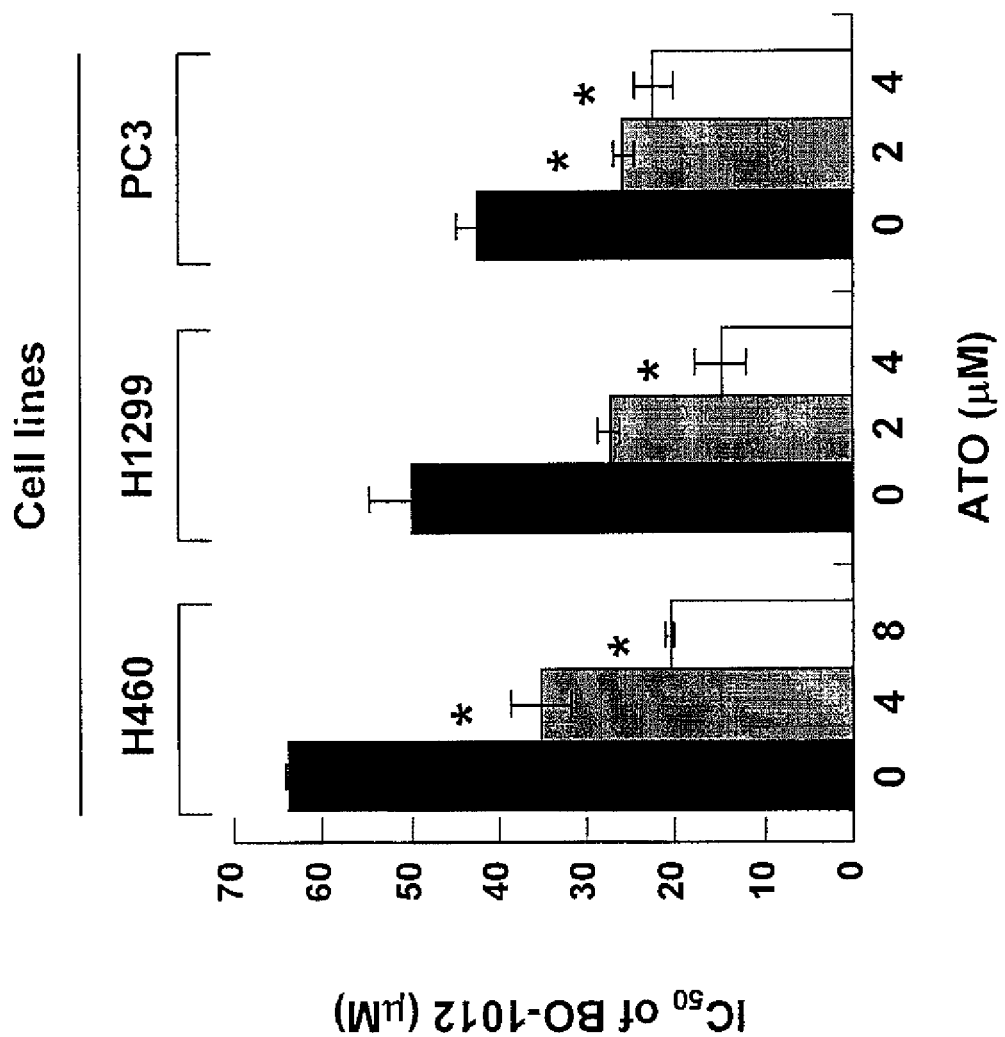
FIG. 2 shows synergistic cytotoxicity of BO-1012 and ATO co-treatment.

To overcome the inherited resistance of H460, H1299, and PC3 cells to these two agents, we co-treated the tumor cell lines with BO-1012 and ATO for 72 h. The IC$_{50}$ values of BO-1012 were significantly reduced by co-treatment with ATO, suggesting that the cytotoxicity of BO-1012 to these inherited resistance cell lines was synergistically enhanced by combining BO-1012 and ATO (FIG. 2). In contrast, co-treatment with BO-1012 and ATO showed no synergistic cytotoxic effect in susceptible cell lines such as OCEM1 and MCF7 cells (data not shown).

Figure 1B:
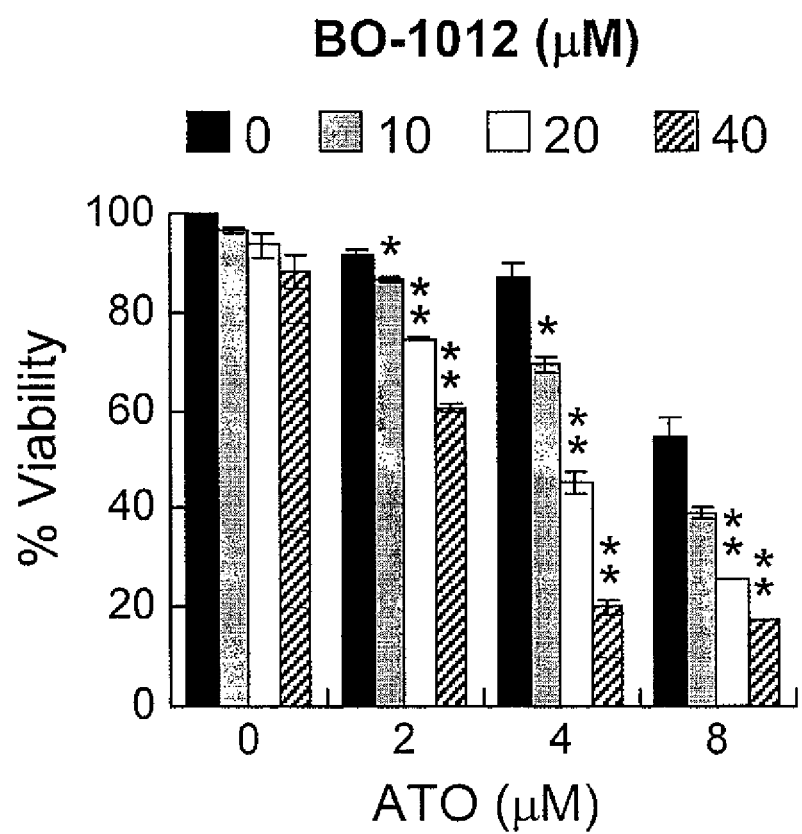
FIG. 1B shows enhanced cytotoxicity in H460 cells treated with a combination of BO-1012 and ATO. H460 cells were treated with BO-1012 for 1 h, washed, and then treated with ATO for 72 h. *, $p<0.05$; **, $p<0.001$ as compared to cells treated with ATO alone.
Figure 1C:
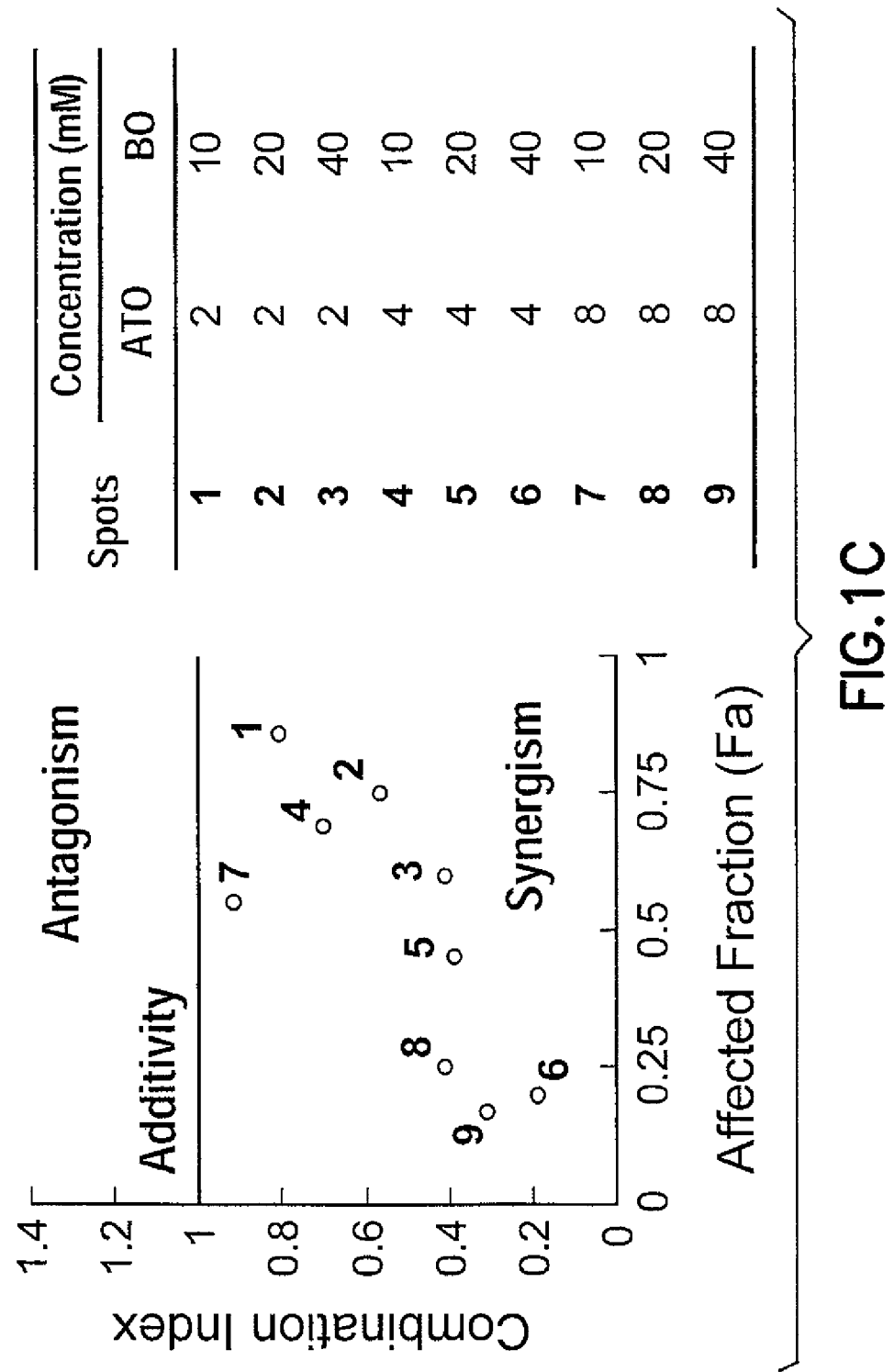
FIG. 1C shows the Fa-CI plot. The isobologram analysis of CI against the affected fraction (Fa) was obtained by the non-constant ratio combination method as described in Materials and Methods. The CIs of all ATO and BO-1012 combinations were <1, indicating synergistic interactions of ATO and BO-1012 in H460 cells.

Because H460 cells were the most resistant to the combination of BO-1012 and ATO, they were used to further study the synergistic effects of these two agents. As shown in FIG. 1B, treatment of H460 cells with 0 to 40 μM BO-1012 for 1 h did not significantly reduce the cell growth rate; however, cell viability decreased substantially when BO-1012-treated H460 cells were subsequently exposed to ATO (0 to 8 μM) for 72 h. The interactions between ATO and BO-1012 were evaluated by the Chou-Talalay combination indices (CI) [39]. The combination indices in all treatments were <1 (FIG. 1C), confirming that treatment with both BO-1012 and ATO had a synergistic cytotoxic effect.

ATO Inhibits Repair of BO-1012-Induced DNA ICLs. Using the alkaline gel shift assay, we confirmed that BO-1012, similar to melphalan and thiotepa, can interact with DNA to form ICLs in vitro (FIG. 3). A modified comet assay was thus adopted to investigate the formation of ICLs in H460 cells treated with BO-1012 and ATO. As shown in FIG. 4A, ICLs increased in a dose-dependent fashion in H460 cells treated with BO-1012, melphalan, or thiotepa for 1 h. BO-1012 induced higher levels of ICLs than melphalan or thiotepa. ATO alone did not cause ICLs (data not shown). However, post-treatment of BO-1012-treated H460 cells with ATO significantly delayed the repair of ICLs (FIG. 4B). The half-life of BO-1012-induced ICLs in H460 cells was ~26.2 h in the absence of ATO, but was ~82.7 h in the presence of ATO. These results indicate that ATO is able to interfere with the repair of ICLs.

ATO Enhances BO-1012-Induced γH2AX Formation. Because ICLs could result in DNA DSBs during DNA replication [41], we determined the effect of combining BO-1012 and ATO on the appearance of a DSB marker, phosphorylated histone H2AX (γH2AX) [42]. Immunofluorescence staining was adopted to examine the formation of γH2AX foci in nuclei (FIGS. 4C,D). Image analysis showed that BO-1012 alone induced γH2AX nuclear foci at 48 h and the number of foci then declined at 72 h; the percentage of cells with γH2AX foci in a total 100 counting cells were 36.5% and 25.9% at 48 and 72 h, respectively, compared to 6.2% and 7.2% in untreated cells. Although BO-1012 treatment for 24 h did not induce formation of γH2AX nuclear foci (5.4%), a large amount of γH2AX was accumulated in the cytosol (FIG. 4C), which is consistent with the increased number of H2AX-positive cells detected at 24 h by flow cytometry (data not shown). ATO alone resulted in only a modest increase in γH2AX foci (26.8%). However, a large number of γH2AX nuclear foci were manifested at 24 h in H460 cells treated with a combination of BO-1012 and ATO. The percentage of cells with γH2AX foci at 24 h was >80%, and declined only slightly at 72 h (60.8%). These results indicate that ATO post-treatment enhanced the conversion of ICLs into DSBs, accelerated the recruitment of γH2AX in nuclei, and interfered with the repair of BO-1012-induced ICLs.

ATO Enhances BO-1012-Induced Cell Cycle Arrest. ATO prolongs the duration of cell cycle perturbation induced by BO-1012 in H460 cells. Because DNA damage may result in inhibition of cell cycle progression, we investigated the effects of BO-1012, ATO, and a combination of both agents on cell cycle progression in H460 cells. After treatment of H460 cells with 10 or 20 μM BO-1012 for 1 h and subsequent treatment with 8 μM ATO for various periods, the cell cycle distribution was analyzed using a flow cytometer. As shown in FIG. 5, 8 μM ATO alone showed a minimal effect on the cell cycle distribution as compared to the untreated control, whereas BO-1012 treatment significantly disturbed cell cycle progression. At the concentrations used, BO-1012 treatment resulted in the accumulation of cells in S phase at 24 h and in G2/M phase at 48 h, and then the cell cycle distribution reverted to the same as seen in the control at 72 h. When BO-1012-treated H460 cells were post-treated with ATO, significant S and G2/M arrests were noticeable at 48 and 72 h, respectively. We infer that the effect of ATO is mediated by inhibiting the repair of BO-1012-induced DNA damage, resulting in prolonged cell cycle delay.

ATO Cooperates with BO-1012 to Augment Induction of Annexin $V^+$ Cells. Apoptosis is usually triggered by DNA damage and cell cycle disturbance. Furthermore, ATO alone has been shown to induce apoptosis [43]. We therefore examined whether BO-1012 induces apoptosis, and whether this effect could be enhanced by post-treatment with ATO. After treatment of H460 cells with BO-1012 for 1 h followed by ATO treatment for 24, 48, and 72 h, an annexin V apoptosis assay was performed, and the percentage of annexin $V^+$ cells was determined by flow cytometry (FIG. 6). FIG. 6A shows a representative flow cytometry histogram of apoptosis. The annexin $V^+$ cells in the top right and bottom right quadrants indicate late and early apoptosis, respectively. As shown in FIG. 6B, the combination of ATO at 8 µM with BO-1012 at 10 or 20 µM was much more effective in inducing annexin cells than either agent alone.

Figure 7A:
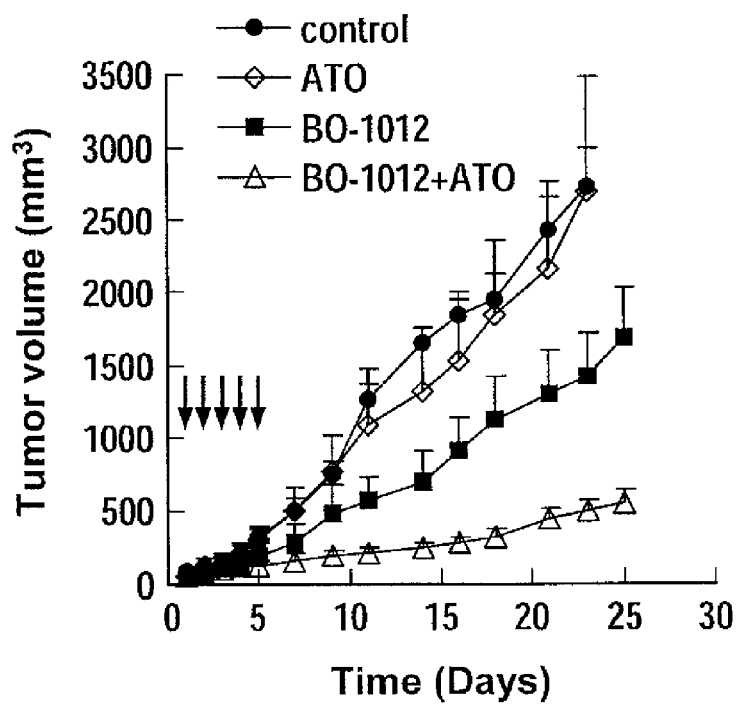

ATO Enhances the Therapeutic Efficacy of BO-1012 in Mice Bearing H460 Tumor Xenografts. The synergistic cytotoxic effect of BO-1012 and ATO in cultured cells drew us to investigate the potential benefit of combining BO-1012 and ATO against inherited resistance H460 cells in a xenograft animal model. H460 cells were subcutaneously inoculated into the hind limb of nude mice. After tumor formation, the mice were treated daily with 2.5 mg/kg BO-1012 and/or 5 mg/kg ATO via i.v. injection for 5 days (QD×5). As shown in FIG. 5A, combined treatment of BO-1012 and ATO significantly suppressed the growth of H460 tumors in nude mice by ~82% (on day 23). BO-1012 and ATO combination treatment induced an obvious tumor growth delay, requiring 23.3 days to achieve a tumor volume of 500 mm$^3$, compared to 7, 7.1, and 9.4 days in untreated control, ATO alone, and BO-1012 alone groups, respectively (FIG. 7A).

Figure 7C:
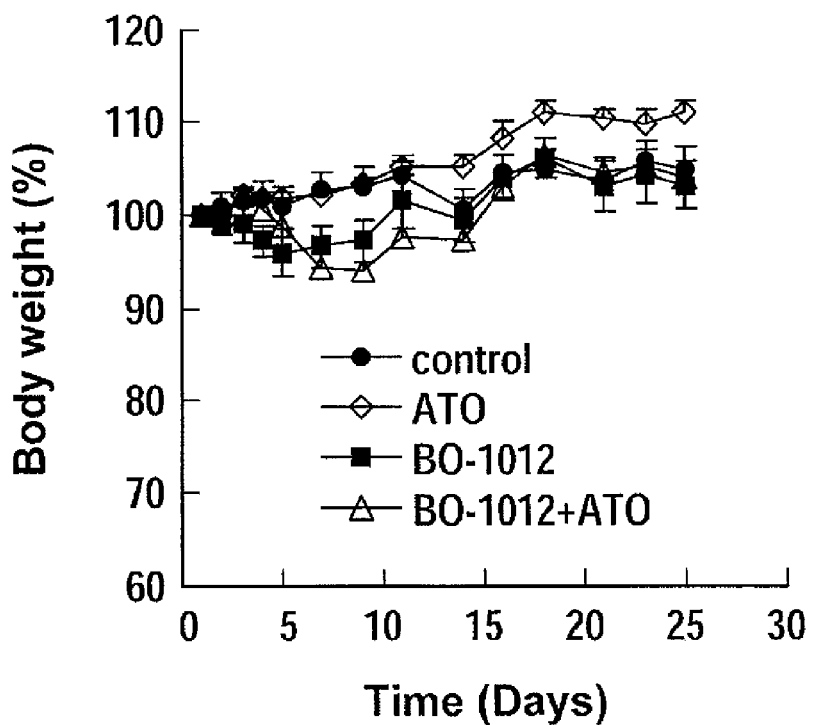
Figure 7B:
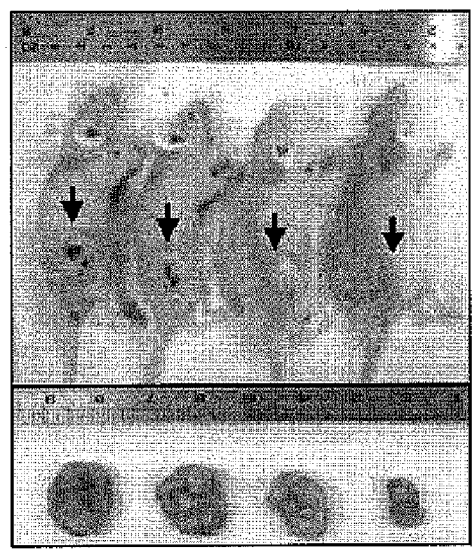

At the end of the experiments (on day 23), the tumor size and weight were determined when the animals were sacrificed. As shown in FIG. 7B, tumor size and weight were synergistically reduced in animals treated with a combination of BO-1012 and ATO as compared to those treated with BO-1012 or ATO alone. The mouse body weight loss, commonly used to evaluate systemic toxicity induced by treatment, was less than 6% in animals treated with BO-1012 alone or BO-1012 plus ATO (FIG. 7C). These results indicate that BO-1012 and its combination with ATO did not cause obvious systemic toxicity.

Figure 7D:
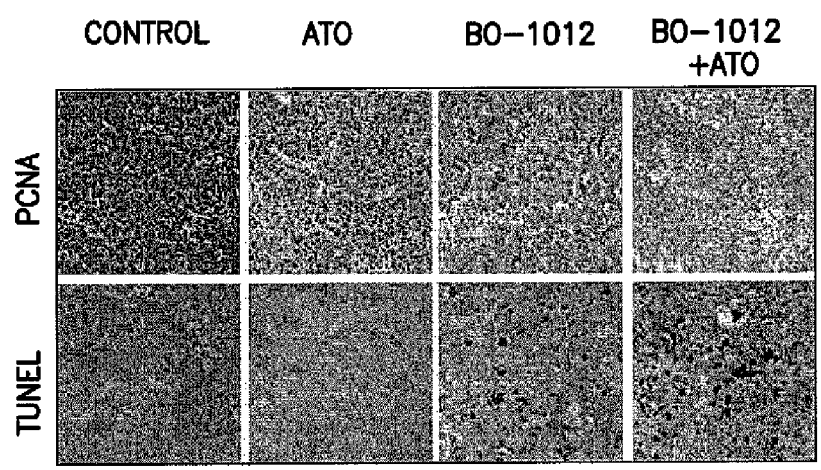

To further examine the anticancer effects of the combination of BO-1012 and ATO, we performed histopathologic evaluation 24 h after the last treatment (i.e., day 6). Using an apoptosis marker level determined by the TUNEL assay, apoptosis was significantly increased in tumors treated with a combination of BO-1012 and ATO. Furthermore, the cell proliferation marker PCNA was markedly suppressed (FIG. 7D). These results indicate that combined treatment of BO-1012 and ATO not only induced apoptotic cell death but also inhibited tumor cell growth substantially.

Figure 8A:
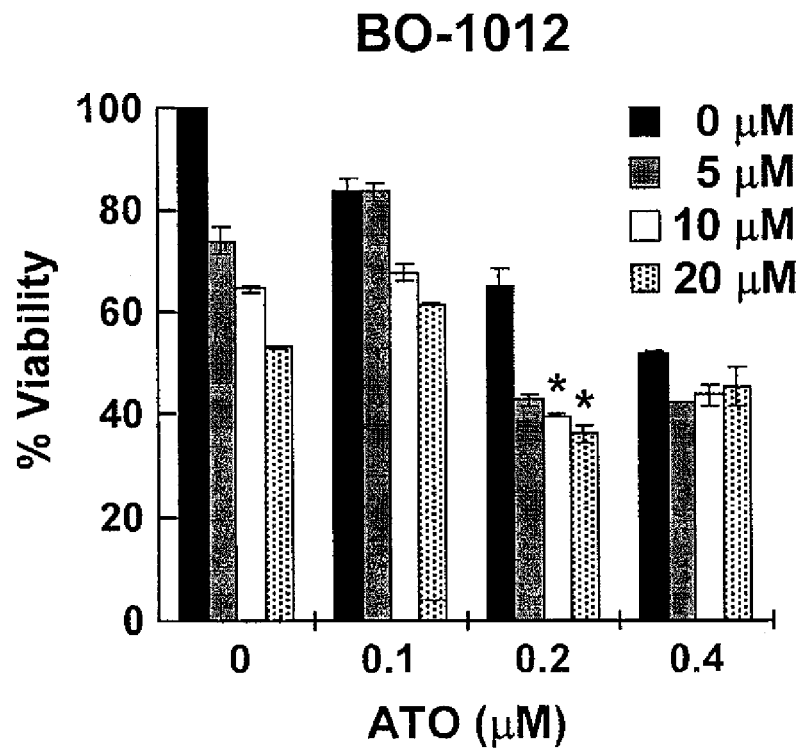
Figure 8B:
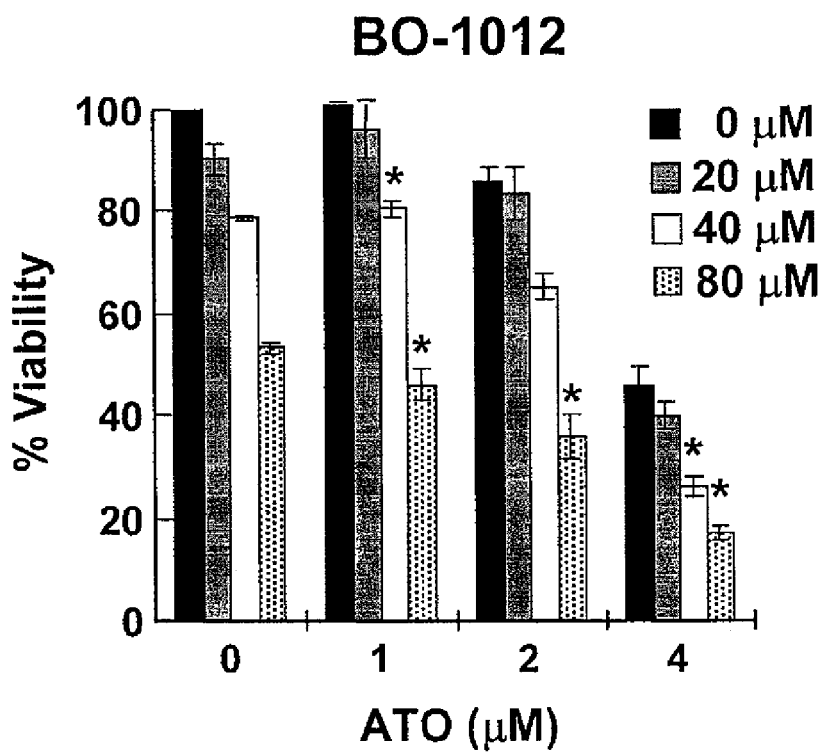
Figure 8D:
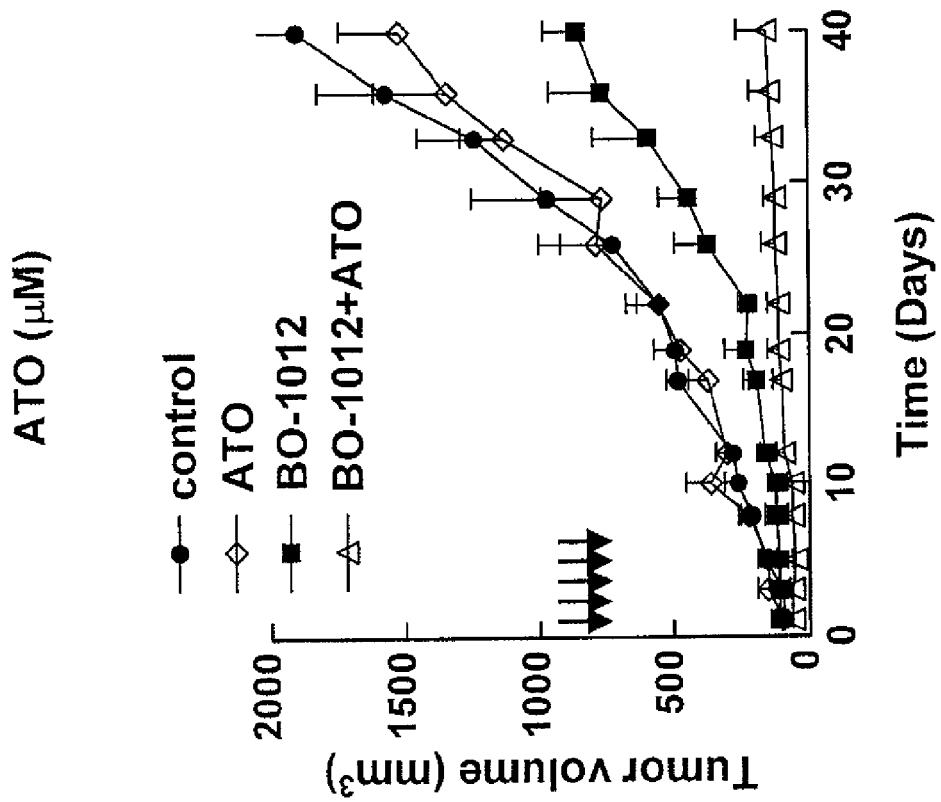
Figure 8C:
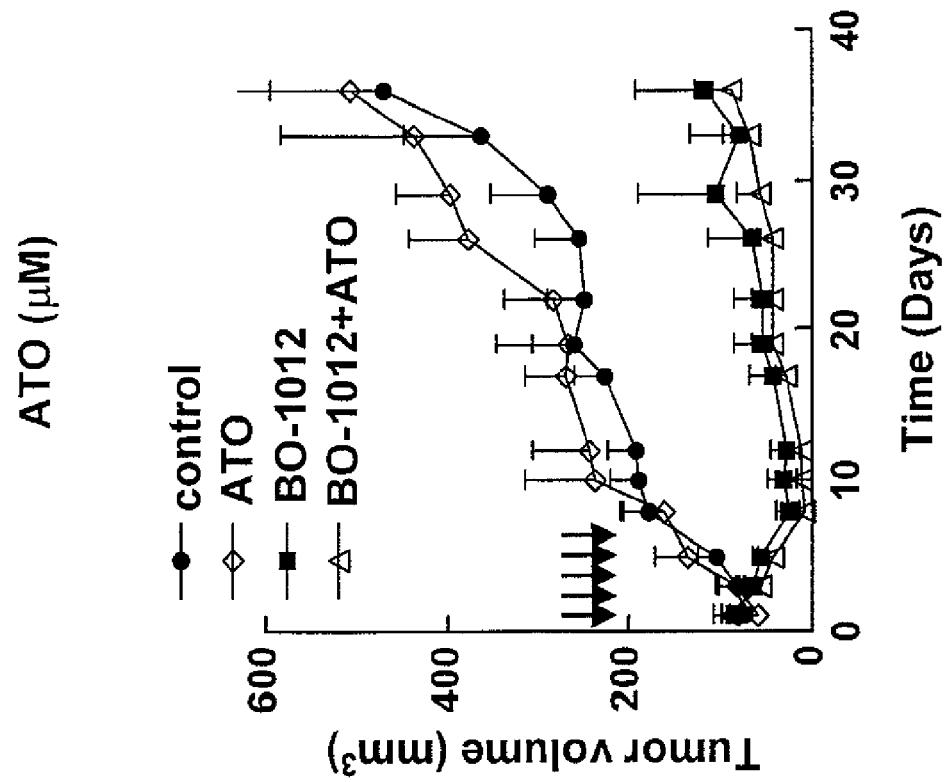

The Combination of ATO and BO-1012 Overcomes Cisplatin-Resistant Bladder Urothelial Carcinoma In Vitro and In vivo. In addition to cells with inherited drug resistance such as H460, we also studied the anticancer effects of treatment with BO-1012 and ATO against cells with acquired drug resistance. NTUB1/P cells, derived from the human bladder urothelial carcinoma cell line NTUB1 [37], are 60-fold more resistant to cisplatin than the parental cells. We confirmed that the $IC_{50}$ values of cisplatin in NTUB1 and NTUB1/P were 3.6 and 211.7 µM, respectively. Besides, we also found that the $IC_{50}$ values of BO-1012 alone against NTUB1 and NTUB1/P were 24.8 and 85.4 µM, whereas the $IC_{50}$ values of ATO alone were 0.4 and 3.8 µM, respectively. Thus, NTUB1/P cells were 3.4- and 9.5-fold more resistant than NTUB1 cells to BO-1012 and ATO, respectively. Using the same treatment protocol as described in FIG. 1B, we observed that there was a significant synergistic effect on inhibition of cell growth in cultures of NTUB1/P cells (FIG. 8B) but not NTUB1 cells (FIG. 8A). To confirm the anticancer activity of combined treatment in an animal model, we treated nude mice bearing NTUB1 or NTUB1/P xenografts with 2.5 mg/kg BO-1012 and/or 5 mg/kg ATO (i.v. injection, QD×5). ATO alone did not effectively suppress the growth of either NTUB1 or NTUB1/P tumors in nude mice (FIGS. 8C and 8D, respectively). In contrast, NTUB1 tumors were nearly completely suppressed by BO-1012, but only a 55% reduction in tumor volume was observed in mice bearing NTUB1/P xenografts. Remarkably, using a combination of BO-1012 and ATO at the same doses, more than 92% reduction of NTUB1/P tumor volume was achieved.

The Combination of BO-1509 and DNA Repair Inhibitor Significantly Suppresses the Growth of Human Lung Adenocarcinoma Cells In vitro and In vivo. While we have demonstrated that ATO could act as DNA repair inhibitor to enhance the antitumor activity of bifunctional alkylating agents, we further confirmed the synergistic cytotoxicity of BO-1509 and LY294002 (PI3K inhibitor) or triciribine (AKT inhibitor) to human lung adenocarcinoma CL-1-5 (FIGS. 9 and 10). At all combination doses tested, the CI values were less than 1, indicating the combination of BO-1059 with inhibitor of PI3K or AKT showed synergistic cell killing effect in cultured lung cancer cells. To confirm the effect of PI3K or AKT inhibitor on DNA repair, we preliminarily performed Western blot assay to analysis the protein levels of Rad51, an essential component involved in homologous recombination repair. As shown in FIG. 11, Rad51 was remarkably enhanced by treatment of CL-1-5 cells with BO-1509, indicating DNA damage induced by BO-1509 significantly activates Rad51. However, Rad-51 activation induced by BO-1509 was almost abolished by the treatment with LY294002, indicating that LY294002 could inhibit the repair of BO-1509-induced DNA damage. Furthermore, our also observed that LY294002 could suppress BO-1509-induced AKT, because negligible amount of pATK was detected in cells treated in combination of BO-1509 and LY294002. In CL-1-5 xenograft model (FIG. 12), our results showed that LY294002 or triciribine (AKTi) alone was unable to suppress the tumor growth at all. BO-1509 by itself caused approximate 70% suppression of tumor growth, while the combination of BO-1509 and LY294002 resulted in >95% suppression (FIG. 12A). The effectiveness of tumor growth suppression in tumor-bearing animals treated combination of BO-1509 and triciribine was similar to BO-1509 alone, indicating that LY2940022 is more effective than triciribine in inhibition of DNA repair. Since there was no significant change in mouse body weight (FIG. 12B), the adverse effects of drug alone or in combination were possibly minimum or tolerable.

Discussion

Either inherited or acquired resistance to chemotherapeutic drugs is a major limitation of therapy for cancer patients. A high capacity for DNA repair in cancer cells is frequently noted as one resistance mechanism [44]. In recent decades, novel therapeutic strategies and drug designs have been of great interest in cancer chemotherapy. The present study is the first to report a potent therapeutic effect using a combination of BO-1012, a newly synthesized MMC derivative [12], and ATO, an agent that inhibits DNA repair. This drug combination strategy effectively suppressed the growth of H460 human large cell lung carcinoma in culture and in a xenograft mouse model as compared to treatment with either agent alone. H460 cells were relatively resistant to several chemotherapeutic treatments, such as BO-1012, ATO (FIG. 1), melphalan, and thiotepa (data not shown), compared to other human solid tumors. Moreover, the therapeutic efficacy in mice bearing H460 xenografts is not convincing using conventional chemotherapy alone or in combination with ionic irradiation; although H460 tumor growth is inhibited during drug treated period, growth rapidly resumes after treatment [45]. H460 cells therefore provide an inherited resistant line for assessing efficacy of new treatments. In this study, we found that a combination of ATO and BO-1012 provided enhanced inhibition of tumor growth of H460 cells compared to BO-1012 alone.

In addition, we evaluated the effectiveness of this drug combination in cells with acquired cisplatin resistance. Platinum chemotherapies have become the most commonly prescribed chemotherapeutic drugs for treating solid cancers in patients [46]. Platinum resistance is a major clinical problem because there are no known drugs that can be used to circumvent this tumor resistance. We found that treatment with ATO in combination with BO-1012 was more effective in inhibiting the growth of an acquired cisplatin-resistant human bladder cancer, NTUB1/P, than was treatment with either single agent. Thus, our study revealed that the combination of a bifunctional alkylating agent and ATO may be an effective regime for treatment of human cancer cells with inherited or acquired drug resistance.

A large number of synthetic and natural bifunctional alkylating agents exhibit anticancer activity because they can induce DNA ICLs [8, 47]. The natural anticancer agent MMC and its analog(s) have been reported to crosslink to DNA double strands [48], and several synthetic bifunctional alkylating agents are under development [12]. However, no studies have reported whether these agents are in clinical trials. The recently synthesized BO-1012 has been demonstrated to be a potent DNA crosslinking agent in human cancers. The mechanism of this agent's anticancer activity is believed to lie in the induction of DNA ICLs and further cellular responses. Once a replication fork stall or collapse is induced by treatment with bifunctional alkylating agents, repair pathways are required to recognize the problem and permit the resumption of replication. When collapsed replication forks are recognized, they trigger cell cycle arrest, DNA repair, or cell death through apoptosis. In the present study, we confirmed that BO-1012 exerts its anticancer effect by inducing DNA ICLs, which may lead to DSBs, cell cycle arrest, and finally cell death. Compared to clinically used melphalan and thiotepa, BO-1012 apparently induces a higher level of ICLs (FIG. 1C and S2) and consequently exhibits potent anticancer activity.

Our present results demonstrate that DNA lesions induced by BO-1012 are still reparable, especially in relatively resistant cancer cells such as H460 cells. The efficacy of anticancer drugs is highly dependent on DNA repair capacity. Numerous studies have shown that cells defective in DNA repair exhibit sensitivity to cancer therapeutic agents such as etoposide, MMC, and ionizing radiation [50]. Unfortunately, a high degree of DNA repair activity is frequently observed in malignant cells, which results in resistance to chemotherapeutic drugs [51]. Inhibition of DNA repair activity is therefore a valuable strategy to enhance the efficacy of anticancer chemotherapeutics. A previous study has reported that resistance to $O^6$-alkylating agents can be overcome by depletion of a DNA repair protein, O-6-methylguanine-DNA methyltransferase (MGMT) [52]. In fact, DNA repair proteins are targets for anticancer drug development [53]. The combination of the DNA damaging agent temozolomide with inhibitors of MGMT is currently under clinical trials [54]. Because arsenic has been reported to impair base excision repair activity by down-regulation of DNA polymerase β. (Pol β) and AP endonuclease [55], and to inhibit PARP-1 [56] and XPA [57] activity through competitive interaction with zinc, we speculate that ATO inhibits DNA repair to enhance the therapeutic effects of DNA damaging agents such as BO-1012. However, how ATO interferes with the repair of ICLs is still unclear.

Emerging evidence has shown that ATO is an effective therapeutic for treatment of patients with relapse/refractory acute promyelocytic leukemia and multiple myeloma, with only mild side effects reported [13,58]. ATO-based chemotherapy is therefore a promising treatment option for patients who tolerate or fail to respond to treatment with other chemotherapy regimens [58]. Because the high doses of ATO used for treatment of solid tumors is associated with clinical risks [59], the combination of ATO with other therapeutic agents may be a good strategy to reduce the ATO dose. In the present study, ATO at subtoxic doses was able to cooperate with BO-1012 to effectively suppress human solid tumor growth.

Recently, a variety of molecular targeted drugs have been developed for patients with malignant disease. Although this type of drug has a high specificity for cancer cells, drug resistance develops frequently and quickly during treatment [60]. Thus, overcoming drug resistance is a challenging issue for the success of cancer therapy. In the present study, as an example, we found that cell lines, such as H460, H1299, PC3, and NTUB1/P cells, that are more resistant to BO-1012 responded well to the addition of ATO. The combined treatment with BO-1012 and ATO, therefore, shows a new route for improving therapeutic efficacy of cancers with inherited or acquired drug resistance.

Besides ATO, numerous compounds targeting component of DNA repair pathways have been in clinical trial for cancer therapies [61]. LY294002 was reported to be able to inhibit DNA repair PI3K or PI3/Akt pathway and possessed antiproliferative and proapoptoic activity in vitro [31]. It was also shown that this agent inhibited tumor growth and induce apoptosis in human tumor cancer xenograft [32,33]. Triciribine was a nucleoside analogue with AKT inhibition activity and was originally found to be a DNA synthesis inhibitor. This nucleoside has been implicated in many human cancers, including prostate carcinomas [34]. Inhibition of AKT was shown to inhibit homologous recombination repair by causing cytoplasmic retention of BRCA1 and Rad51 [62]. Based on our current results, we have discovered that these DNA repair inhibitors may enhance the anticancer efficacy of alkylating agents mediated through its inhibitory activity on the repair of DNA damages induced by alkylating agents. Since the enhanced DNA repair activity is frequently observed in a variety of drug resistant cancer cells, the combination may be particularly effective to conquer drug resistant cells.

REFERENCES

1. Wadhwa, P. D., Zielske, S. P., Roth, J. C., Ballas, C. B., Bowman, J. E. and Gerson, S. L. (2002) Cancer gene therapy: scientific basis. *Annu Rev Med*, 53, 437-52.
2. Ariel, I. M. (1957) Treatment of inoperable cancer by intra-arterial administration of mechlorethamine. *AMA Arch Surg*, 74, 516-24.
3. Musto, P. and D'Auria, F. (2007) Melphalan: old and new uses of a still master drug for multiple myeloma. *Expert Opin Investig Drugs*, 16, 1467-87.

4. La Rocca, R. V. and Mehdorn, H. M. (2009) Localized BCNU chemotherapy and the multimodal management of malignant glioma. *Curr Med Res Opin*, 25, 149-60.
5. Ciurea, S. O. and Andersson, B. S. (2009) Busulfan in hematopoietic stem cell transplantation. *Biol Blood Marrow Transplant*, 15, 523-36.
6. Valteau-Couanet, D., Fillipini, B., Benhamou, E., Grill, J., Kalifa, C., Couanet, D., Habrand, J. L. and Hartmann, O. (2005) High-dose busulfan and thiotepa followed by autologous stem cell transplantation (ASCT) in previously irradiated medulloblastoma patients: high toxicity and lack of efficacy. *Bone Marrow Transplant*, 36, 939-45.
7. Knipp, M. (2009) Metallothioneins and platinum(II) antitumor compounds. *Curr Med Chem*, 16, 522-37.
8. Hofheinz, R. D., Beyer, U., Al-Batran, S. E. and Hartmann, J. T. (2008) Mitomycin C in the treatment of gastrointestinal tumours: recent data and perspectives. *Onkologie*, 31, 271-81.
9. McHugh, P. J., Spanswick, V. J. and Hartley, J. A. (2001) Repair of DNA interstrand crosslinks: molecular mechanisms and clinical relevance. *Lancet Oncol*, 2, 483-90.
10. Heckman, J. E., Lambert, D. and Burke, J. M. (2005) Photocrosslinking detects a compact, active structure of the hammerhead ribozyme. *Biochemistry*, 44, 4148-56.
11. Collis, S. J., Barber, L. J., Ward, J. D., Martin, J. S. and Boulton, S. J. (2006) C. elegans FANCD2 responds to replication stress and functions in interstrand cross-link repair. *DNA Repair (Amst)*, 5, 1398-406.
12. Kakadiya, R., Dong, H., Lee, P. C., Kapuriya, N., Zhang, X., Chou, T. C., Lee, T. C., Kapuriya, K., Shah, A. and Su, T. L. (2009) Potent antitumor bifunctional DNA alkylating agents, synthesis and biological activities of 3a-aza-cyclopenta[a]indenes. *Bioorg Med Chem*.
13. Soignet, S. L., Frankel, S. R., Douer, D., Tallman, M. S., Kantarjian, H., Calleja, E., Stone, R. M., Kalaycio, M., Scheinberg, D. A., Steinherz, P., Sievers, E. L., Coutre, S., Dahlberg, S., Ellison, R. and Warrell, R. P., Jr. (2001) United States multicenter study of arsenic trioxide in relapsed acute promyelocytic leukemia. *J Clin Oncol*, 19, 3852-60.
14. Maeda, H., Hori, S., Nishitoh, H., Ichijo, H., Ogawa, O., Kakehi, Y. and Kakizuka, A. (2001) Tumor growth inhibition by arsenic trioxide (As2O3) in the orthotopic metastasis model of androgen-independent prostate cancer. *Cancer Res*, 61, 5432-40.
15. Kito, M., Matsumoto, K., Wada, N., Sera, K., Futatsugawa, S., Naoe, T., Nozawa, Y. and Akao, Y. (2003) Antitumor effect of arsenic trioxide in murine xenograft model. *Cancer Sci*, 94, 1010-4.
16. Vuky, J., Yu, R., Schwartz, L. and Motzer, R. J. (2002) Phase II trial of arsenic trioxide in patients with metastatic renal cell carcinoma. *Invest New Drugs*, 20, 327-30.
17. Kim, K. B., Bedikian, A. Y., Camacho, L. H., Papadopoulos, N. E. and McCullough, C. (2005) A phase II trial of arsenic trioxide in patients with metastatic melanoma. *Cancer*, 104, 1687-92.
18. Qian, J., Qin, S, and He, Z. (2001) [Arsenic trioxide in the treatment of advanced primary liver and gallbladder cancer]. *Zhonghua thong Liu Za Zhi*, 23, 487-9.
19. Han, Y. H., Kim, S. Z., Kim, S. H. and Park, W. H. (2008) Induction of apoptosis in arsenic trioxide-treated lung cancer A549 cells by buthionine sulfoximine. *Mol Cells*, 26, 158-64.
20. Lin, Y. L., Ho, I. C., Su, P. F. and Lee, T. C. (2006) Arsenite pretreatment enhances the cytotoxicity of mitomycin C in human cancer cell lines via increased NAD(P)H quinone oxidoreductase 1 expression. *Toxicol Appl Pharmacol*, 214, 309-17.
21. Lee, T. C., Huang, R. Y. and Jan, K. Y. (1985) Sodium arsenite enhances the cytotoxicity, clastogenicity, and 6-thioguanine-resistant mutagenicity of ultraviolet light in Chinese hamster ovary cells. *Mutat Res*, 148, 83-9.
22. Wang, W., Qin, S. K., Chen, B. A. and Chen, H. Y. (2001) Experimental study on antitumor effect of arsenic trioxide in combination with cisplatin or doxorubicin on hepatocellular carcinoma. *World J Gastroenterol*, 7, 702-5.
23. Chun, Y. J., Park, I. C., Park, M. J., Woo, S. H., Hong, S. I., Chung, H. Y., Kim, T. H., Lee, Y. S., Rhee, C. H. and Lee, S. J. (2002) Enhancement of radiation response in human cervical cancer cells in vitro and in vivo by arsenic trioxide (As2O3). *FEBS Lett*, 519, 195-200.
24. Qazilbash, M. H., Saliba, R. M., Nieto, Y., Parikh, G., Pelosini, M., Khan, F. B., Jones, R. B., Hosing, C., Mendoza, F., Weber, D. M., Wang, M., Popat, U., Alousi, A., Anderlini, P., Champlin, R. E. and Giralt, S. (2008) Arsenic trioxide with ascorbic acid and high-dose melphalan: results of a phase II randomized trial. *Biol Blood Marrow Transplant*, 14, 1401-7.
25. Campbell, R. A., Sanchez, E., Steinberg, J. A., Baritaki, S., Gordon, M., Wang, C., Shalitin, D., Chen, H., Pang, S., Bonavida, B., Said, J. and Berenson, J. R. (2007) Antimyeloma effects of arsenic trioxide are enhanced by melphalan, bortezomib and ascorbic acid. *Br J Haematol*, 138, 467-78.
26. Ning, S, and Knox, S. J. (2006) Optimization of combination therapy of arsenic trioxide and fractionated radiotherapy for malignant glioma. *Int J Radiat Oncol Biol Phys*, 65, 493-8.
27. Lee, T. C., Kao, S. L. and Yih, L. H. (1991) Suppression of sodium arsenite-potentiated cytotoxicity of ultraviolet light by cycloheximide in Chinese hamster ovary cells. *Arch Toxicol*, 65, 640-5.
28. Walter, I., Schwerdtle, T., Thuy, C., Parsons, J. L., Dianov, G. L. and Hartwig, A. (2007) Impact of arsenite and its methylated metabolites on PARP-1 activity, PARP-1 gene expression and poly(ADP-ribosyl)ation in cultured human cells. *DNA Repair (Amst)*, 6, 61-70.
29. Andrew, A. S., Burgess, J. L., Meza, M. M., Demidenko, E., Waugh, M. G., Hamilton, J. W. and Karagas, M. R. (2006) Arsenic exposure is associated with decreased DNA repair in vitro and in individuals exposed to drinking water arsenic. *Environ Health Perspect*, 114, 1193-8.
30. Hartwig, A., Blessing, H., Schwerdtle, T. and Walter, I. (2003) Modulation of DNA repair processes by arsenic and selenium compounds. *Toxicology*, 193, 161-9.
31. Wetzker, R. and Rommel, C. (2004) Phosphoinositide 3-kinases as targets for therapeutic intervention. *Curr Pharm Des*, 10, 1915-22.
32. Semba, S., Itoh, N., Ito, M., Harada, M. and Yamakawa, M. (2002) The in vitro and in vivo effects of 2-(4-morpholinyl)-8-phenyl-chromone (LY294002), a specific inhibitor of phosphatidylinositol 3'-kinase, in human colon cancer cells. *Clin Cancer Res*, 8, 1957-63.
33. Fan, Q. W., Specht, K. M., Zhang, C., Goldenberg, D. D., Shokat, K. M. and Weiss, W. A. (2003) Combinatorial efficacy achieved through two-point blockade within a signaling pathway—a chemical genetic approach. *Cancer Res*, 63, 8930-8.
34. Dieterle, A., Orth, R., Daubrawa, M., Grotemeier, A., Alers, S., Ullrich, S., Lammers, R., Wesselborg, S, and Stork, B. (2009) The Akt inhibitor triciribine sensitizes prostate carcinoma cells to TRAIL-induced apoptosis. *Int J Cancer*, 125, 932-41.
35. Chou, T. C. and Talalay, P. (1984) Quantitative analysis of dose-effect relationships: the combined effects of multiple drugs or enzyme inhibitors. *Adv Enzyme Regul*, 22, 27-55.
36. Lai, K. C., Chang, K. W., Liu, C. J., Kao, S. Y. and Lee, T. C. (2008) IFN-induced protein with tetratricopeptide repeats 2 inhibits migration activity and increases survival of oral squamous cell carcinoma. *Mol Cancer Res*, 6, 1431-9.
37. Yu, H. J., Tsai, T. C., Hsieh, T. S, and Chiu, T. Y. (1992) Characterization of a newly established human bladder carcinoma cell line, NTUB1. *J Formos Med Assoc*, 91, 608-13.
38. Pu, Y. S., Hour, T. C., Chen, J., Huang, C. Y., Guan, J. Y. and Lu, S. H. (2002) Cytotoxicity of arsenic trioxide to transitional carcinoma cells. *Urology*, 60, 346-50.
39. Chou, T. C. (2006) Theoretical basis, experimental design, and computerized simulation of synergism and antagonism in drug combination studies. *Pharmacol Rev*, 58, 621-81.
40. Yih, L. H., Tseng, Y. Y., Wu, Y. C. and Lee, T. C. (2006) Induction of centrosome amplification during arsenite-induced mitotic arrest in CGL-2 cells. *Cancer Res*, 66, 2098-106.
41. Lopes, M., Cotta-Ramusino, C., Pellicioli, A., Liberi, G., Plevani, P., Muzi-Falconi, M., Newlon, C. S, and Foiani, M. (2001) The DNA replication checkpoint response stabilizes stalled replication forks. *Nature*, 412, 557-61.
42. Fernandez-Capetillo, 0., Allis, C. D. and Nussenzweig, A. (2004) Phosphorylation of histone H2B at DNA double-strand breaks. *J Exp Med*, 199, 1671-7.
43. Kang, Y. H., Yi, M. J., Kim, M. J., Park, M. T., Bae, S., Kang, C. M., Cho, C. K., Park, I. C., Park, M. J., Rhee, C. H., Hong, S. I., Chung, H. Y., Lee, Y. S, and Lee, S. J. (2004) Caspase-independent cell death by arsenic trioxide in human cervical cancer cells: reactive oxygen species-mediated poly (ADP-ribose) polymerase-1 activation signals apoptosis-inducing factor release from mitochondria. *Cancer Res*, 64, 8960-7.
44. Friesen, C., Lubatschofski, A., Kotzerke, J., Buchmann, I., Reske, S. N. and Debatin, K. M. (2003) Beta-irradiation used for systemic radioimmunotherapy induces apoptosis and activates apoptosis pathways in leukaemia cells. *Eur J Nucl Med Mol Imaging*, 30, 1251-61.
45. Carter, C. A., Chen, C., Brink, C., Vincent, P., Maxuitenko, Y. Y., Gilbert, K. S., Waud, W. R. and Zhang, X. (2007) Sorafenib is efficacious and tolerated in combination with cytotoxic or cytostatic agents in preclinical models of human non-small cell lung carcinoma. *Cancer Chemother Pharmacol*, 59, 183-95.
46. Rosenberg, B., VanCamp, L., Trosko, J. E. and Mansour, V. H. (1969) Platinum compounds: a new class of potent antitumour agents. *Nature*, 222, 385-6.
47. Tomasz, M. and Palom, Y. (1997) The mitomycin bioreductive antitumor agents: cross-linking and alkylation of DNA as the molecular basis of their activity. *Pharmacol Ther*, 76, 73-87.
48. Plumb, J. A. and Workman, P. (1994) Unusually marked hypoxic sensitization to indoloquinone EO9 and mitomycin C in a human colon-tumour cell line that lacks DT-diaphorase activity. *Int J Cancer*, 56, 134-9.
49. Sorensen, C. S., Hansen, L. T., Dziegielewski, J., Syljuasen, R. G., Lundin, C., Bartek, J. and Helleday, T. (2005) The cell-cycle checkpoint kinase Chk1 is required for mammalian homologous recombination repair. *Nat Cell Biol*, 7, 195-201.
50. Thompson, L. H. (1999) Strategies for cloning mammalian DNA repair genes. *Methods Mol Biol*, 113, 57-85.
51. Chabner, B. A. and Roberts, T. G., Jr. (2005) Timeline: Chemotherapy and the war on cancer. *Nat Rev Cancer*, 5, 65-72.
52. Gerson, S. L., Berger, N. A., Arce, C., Petzold, S. J. and Willson, J. K. (1992) Modulation of nitrosourea resistance in human colon cancer by O6-methylguanine. *Biochem Pharmacol*, 43, 1101-7.
53. Helleday, T., Petermann, E., Lundin, C., Hodgson, B. and Sharma, R. A. (2008) DNA repair pathways as targets for cancer therapy. *Nat Rev Cancer*, 8, 193-204.
54. Quinn, J. A., Jiang, S. X., Reardon, D. A., Desjardins, A., Vredenburgh, J. J., Gururangan, S., Sampson, J. H., McLendon, R. E., Herndon, J. E., 2nd and Friedman, H. S. (2009) Phase 1 trial of temozolomide plus irinotecan plus O6-benzylguanine in adults with recurrent malignant glioma. *Cancer*, 115, 2964-70.
55. Sykora, P. and Snow, E. T. (2008) Modulation of DNA polymerase beta-dependent base excision repair in cultured human cells after low dose exposure to arsenite. *Toxicol Appl Pharmacol*, 228, 385-94.
56. Qin, X. J., Hudson, L. G., Liu, W., Timmins, G. S, and Liu, K. J. (2008) Low concentration of arsenite exacerbates UVR-induced DNA strand breaks by inhibiting PARP-1 activity. *Toxicol Appl Pharmacol*, 232, 41-50.
57. Mustra, D. J., Warren, A. J., Wilcox, D. E. and Hamilton, J. W. (2007) Preferential binding of human XPA to the mitomycin C-DNA interstrand crosslink and modulation by arsenic and cadmium. *Chem Biol Interact*, 168, 159-68.
58. Berenson, J. R. and Yeh, H. S. (2006) Arsenic compounds in the treatment of multiple myeloma: a new role for a historical remedy. *Clin Lymphoma Myeloma*, 7, 192-8.
59. Westervelt, P., Brown, R. A., Adkins, D. R., Khoury, H., Curtin, P., Hurd, D., Luger, S. M., Ma, M. K., Ley, T. J. and DiPersio, J. F. (2001) Sudden death among patients with acute promyelocytic leukemia treated with arsenic trioxide. *Blood*, 98, 266-71.
60. Nguyen, K. S., Kobayashi, S, and Costa, D. B. (2009) Acquired resistance to epidermal growth factor receptor tyrosine kinase inhibitors in non-small-cell lung cancers dependent on the epidermal growth factor receptor pathway. *Clin Lung Cancer*, 10, 281-9.
61. Bolderson, E., Richard, D. J., Zhou, B. B. and Khanna, K. K. (2009) Recent advances in cancer therapy targeting proteins involved in DNA double-strand break repair. *Clin Cancer Res*, 15, 6314-20.
62. Plo, I., Laulier, C., Gauthier, L., Lebrun, F., Calvo, F. and Lopez, B. S. (2008) AKT1 inhibits homologous recombination by inducing cytoplasmic retention of BRCA1 and RAD51. *Cancer Res*, 68, 9404-12.

What is claimed is:

1. A pharmaceutical composition for treating cancer comprising an effective amount of a derivative of 3a-aza-cyclopentaindene selected from the group consisting of BO-1012, an effective amount of a DNA repair inhibitor, and a pharmaceutically acceptable carrier.

2. The composition of claim 1 wherein the DNA repair inhibitor is selected from the group consisting of arsenic trioxide, LY294002, and triciribine.

3. A method of treating cancer suffered by a mammalian subject comprising administering to the subject an effective amount of BO-1012 and an effective amount of a DNA repair inhibitor.

4. The method of claim 3 wherein the subject is administered with the BO-1012 before being administered with the DNA repair inhibitor.

5. The method of claim 3 wherein the DNA repair inhibitor is selected from the group consisting of ATO, Ly294002, and triciribine.

6. The method of claim 3 wherein the cancer is resistant to an individual therapeutic agent.

7. The method of claim 3 wherein the cancer is human lung cancer.

8. The method of claim 3 wherein the cancer is human bladder cancer.

9. The method of claim 3 wherein the cancer is human breast cancer.

10. The method of claim 3 wherein the cancer is human prostate cancer.

11. The method of claim 3 wherein the cancer is human glioma cancer.

12. The method of claim 3 wherein the cancer is human oral cancer.

13. A pharmaceutical composition for treating cancer comprising an effective amount of BO-1509, an effective amount of a DNA repair inhibitor, and a pharmaceutically acceptable carrier.

14. The composition of claim 13 wherein the DNA repair inhibitor is selected from the group consisting of arsenic trioxide, LY294002, and triciribine.

* * * * *